United States Patent [19]
Karimian et al.

[11] Patent Number: 6,162,791
[45] Date of Patent: Dec. 19, 2000

[54] THIADIAZOLE COMPOUNDS USEFUL AS INHIBITORS OF CYSTEINE ACTIVITY DEPENDENT ENZYMES

[75] Inventors: Khashayar Karimian, Mississauga; Tim Fat Tam, Woodbridge; Regis C. S. H. Leung-Toung, Mississauga; Wanren Li, Etobicoke, all of Canada

[73] Assignee: Apotex Inc., Weston, Canada

[21] Appl. No.: 09/033,937

[22] Filed: Mar. 2, 1998

[51] Int. Cl.[7] .......................... A61K 31/41; C07D 285/68
[52] U.S. Cl. ........................... 514/19; 514/361; 548/128; 548/130
[58] Field of Search ................................... 548/130, 128; 514/19, 361

[56] References Cited

U.S. PATENT DOCUMENTS 5,036,085   7/1991   Heinemann ............................ 514/361

*Primary Examiner*—Robert Gerstl
*Attorney, Agent, or Firm*—Nixon & Vanderhye P.C.

[57] ABSTRACT

Novel 1,2,4-thiadiazole compounds are provided, which are effective as inhibitors of cysteine activity-dependent enzymes and in particular of cysteine proteases. The compounds are useful in treating acne by inhibition of transglutaminase, common cold by inhibition of human rhinovirus 3C protease and inflammatory joint disease by inhibition of cathepsins. The compounds of the present invention are 3,5-disubstituted 1,2,4-thiadazole of the general formula (I):

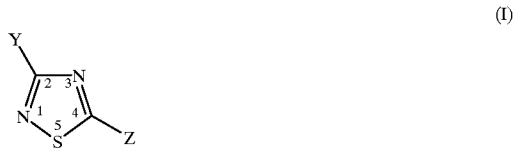

(I)

where Z is a nitrogen containing group with recognition sequence for the enzyme and Y is a substituent that tunes the reactivity of the inhibitor towards the thiol group of the cysteine activity-dependent enzyme. The Y group may also serve in recognition.

42 Claims, 2 Drawing Sheets

Effect of APO501 on IL-1-induced Proteoglycan Degradation

THIADIAZOLE COMPOUNDS USEFUL AS INHIBITORS OF CYSTEINE ACTIVITY DEPENDENT ENZYMES

FIELD OF THE INVENTION

This invention relates to novel compounds and their pharmaceutically acceptable acid addition salts and base addition salts for use in the treatment of acne, common cold, inflammatory joint disease by inhibition of cysteine proteases and cysteine activity dependent enzymes. In particular, it relates to novel compounds having pharmaceutical utility, to processes for their preparation, to compositions and uses in the treatment of various diseases by inhibition of cysteine proteases and cysteine activity dependent enzymes.

BACKGROUND OF THE INVENTION AND PRIOR ART

Transglutaminase, rhinovirus 3C protease, calpain, interleukin beta converting enzyme, cathepsin B are examples of cysteine activity-dependent enzymes which are involved in the progression of various disorders and/or diseases such as acne, common cold and arthritis. These enzymes include in their chemical structure cysteine residues. It is believed that the thiol group of a cysteine residue in the enzyme acts as a nucleophile and causes the hydrolysis of the substrate thus permitting the progression of the disorder and/or disease. Accordingly, attempts have been made to develop thiol trapping agents to inhibit the catalytic activity of such enzymes in order to prevent the progression of the disease. Hagiwara reported the use of 1,2,4-thiadiazolines as inhibitors of alcohol dehydrogenase, a cysteine activity dependent enzyme.

U.S. Pat. No. 5,618,792 disclosed certain 3-substituted oxadiazole and 3-substituted thiadiazole peptoids which are serine protease inhibitors. U.S. Pat. No. 4,207,090 disclosed amino ester derivatives of 3-trihalomethyl-[1,2,4]-thiadiazoles as pesticides. U.S. Pat. No. 5,677,302 discloses the use of 1,2,4-thiadiazole [4,5-a] benzimidazoles and imidazo [1,2-d]-1,2,4-thiadiazoles as inhibitors of the enzyme $H^+/K^+$-ATPase, also known as the proton pump, another cysteine activity dependent enzyme. Condensed thiadiazole derivatives having a sulfonylimino group have been disclosed in U.S. Pat. No. 5,550,138 as being cathepsin B inhibitors. The various peptidyl inhibitors of cysteine proteases have been reviewed in protein profile, 1995, Vol. 2, issue 14, p. 1587–1591. Unfortunately, most of the efforts have been largely frustrated by the reactivity of potential inhibitors with other nucleophiles such as alcohols and amines which are abundant in physiological systems.

The development of compounds which exhibits selective reactivity towards the thiol group of a cysteine of the cysteine activity dependent enzyme residue will represent an enormous advance in this field.

SUMMARY OF THE INVENTION

It is an object of the present invention to provide novel pharmaceutical compounds, and composition containing such compounds which are active as cysteine activity dependent enzyme inhibitors and hence useful in the treatment of disorder and/or disease caused by the activity of such enzymes, and in particular transglutaminase human, rhinovirus 3C protease and cathepsin B.

It is a further object of the invention to provide processes for the synthesis of such compounds.

Thus according to the present invention there are provided compounds having the following general formula (I);

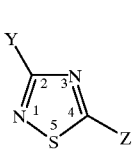

(I)

or their pharmaceutically acceptable salts thereof, with the proviso that Y is not trifluoromethyl or trichloromethyl;

wherein:

Z is selected from the groups:

(a) —A—W; in which A is an amino acid residue, or a peptide containing 2 to 3 amino acid residues or an isosteric form thereof and W represents a group of formula —N($R^1$)$_2$ or —$OR^1$ with $R^1$ being independently hydrogen, lower alkyl, lower alkenyl, lower alkynyl in which the unsaturated bond is at least one carbon removed from the N or O atom;

(b) —X—A—W; in which X is a spacer selected from the groups of formula

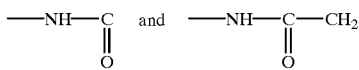

and A, W have the same definition as above;

(c)

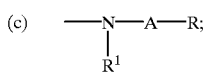

wherein R represents hydrogen, lower alkanoyl, lower cycloalkylcarbonyl, lower alkoxycarbonyl, lower arylalkyloxycarbonyl or N-protecting group and $R^1$, A have the same definition as above;

with the proviso that in:

groups (a) and (b), the N-terminal of A is either directly attached or by means of a spacer X as defined above to the C5 of the 1,2,4-thiadiazole ring respectively; and group (c), the carboxyl terminal of A is directly attached to the nitrogen of the 5-amino-1,2,4-thiadiazole;

and Y is selected from:

(1) lower alkoxy, lower cycloalkoxy, lower arylalkoxy, heterocyclyloxy, and lower heterocyclylalkoxy wherein the alkyl or aryl ring is optionally substituted with 1 to 2 substituents selected from the group amino, alkoxy, hydroxy, halo, amino, alkylamino, dialkylamino;

(2) lower alkyl, lower cycloalkyl, lower heterocyclylalkyl, heterocyclyl, aryl, lower arylalkyl, lower arylalkenyl, lower heterocyclylalkenyl wherein the alkyl or aryl ring is optionally substituted with 1 to 2 substituents selected from the group amino, alkoxy, hydroxy, halo, amino, alkylamino, and dialkylamino;

(3) lower alkoxycarbonyl, carboxyl;

(4) a ketone group of formula:

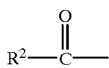

in which R² represents lower alkyl, lower cycloalkyl, lower heterocyclylalkyl, heterocyclyl, aryl, lower arylalkyl wherein the alkyl or aromatic ring is optionally substituted with 1 to 2 substituents selected from the group amino, alkoxy, hydroxy, halo, amino, alkylamino, dialkylamino;

(5) a carbamoyl group of formula:

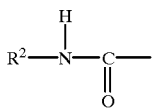

with R² being as defined above;

(6) amino, lower alkylamino, lower dialkylamino;

(7) amide of formula:

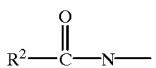

with R² being as defined above;

(8) a group of formula:

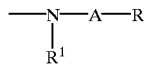

wherein A is as defined above and the carboxyl terminal of A is directly attached to the nitrogen of the 3-amino-1,2,4-thiadiazole. R and R¹ being as defined above;

(9) alcohol of formula:

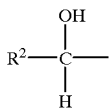

with R² being as defined above;

(10) sulfone of formula:

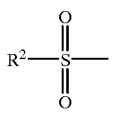

with R² being as defined above;

(11) sulfoxide of formula:

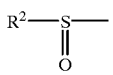

with R² being as defined above;

(12) sulfonamide of formula:

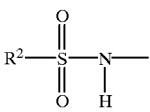

with R² being as defined above;

(13) lower alkylthio, lower arylalkylthio, arylthio;

(14) a group of formula:

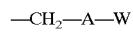

—CH₂—A—W with A as defined above and the N-terminal of A is directly attached to the methylene and W being as defined above.

(15) a group of formula:

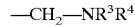

—CH₂—NR³R⁴ in which R³ and R⁴ are independently alkyl, aralkyl, heterocyclyl, heterocyclylalkyl; R³ and R⁴ when taken together form with the N-atom a five or a six membered ring selected from the group piperidinyl, pyrrolidinyl, piperazinyl with the N-4 position of piperazine optionally substituted with pyridyl, heterocyclyl, alkyl, aralkyl and aryl.

BRIEF REFERENCE TO THE DRAWINGS

DESCRIPTION OF THE PREFERRED EMBODIMENTS

One class of preferred compounds according to the invention are compounds corresponding to the following formula (II):

or their pharmaceutically acceptable salts thereof, wherein:

A, W and Y are as previously defined.

A second class of preferred compounds according to the present invention are compounds having the general formula (III):

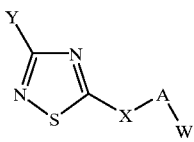

(III)

or their pharmaceutically acceptable salts thereof, wherein X, A, W and Y are as previously defined.

A further class of preferred compounds according to the present invention are compounds having the general formula (IV).

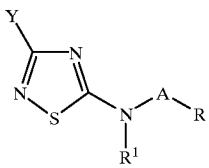

(IV)

or their pharmaceutically acceptable salts thereof, wherein:

A, R, $R_1$ and Y are as previously defined.

While the mechanism of action for all these compounds has not been confirmed, it is believed that the 3,5 disubstituted -1,2,4-thiadiazoles of the present invention react with the cysteine residue of the enzyme to form a disulfide bond thus inhibiting the activity of the enzyme. The S—N bond in the 3,5 disubstituted -1,2,4-thiadiazoles of the present invention has a high energy content which originates, at least in part, from non-bonded electron repulsion between sulfur atom d orbitals and nitrogen atom p orbitals. 3,5 disubstituted -1,2,4-thiadiazoles are therefore likely to be susceptible to nucleophilic attack. S—N bond cleavage of 1,2,4-thiadiazoles with reducing agents was reported over forty years ago (Gordeler, Chem. Ber., 1954, 87, 57). The thiol groups of cysteine dependent enzymes appear to act as reducing agents (nucleophiles), thereby becoming chemically modified with resulting inhibition of the enzymatic activity.

Group Z at the C-5 position of the 1,2,4-thiadiazoles can be designed to incorporate a recognition sequence specific to the active site of a given cysteine activity dependent enzyme and group Y at the C-3 position may be designed to tune the reactivity of the 5-substituted 1,2,4-thiadiazoles towards the enzyme by activating the adjacent bonds.

Figure 1:
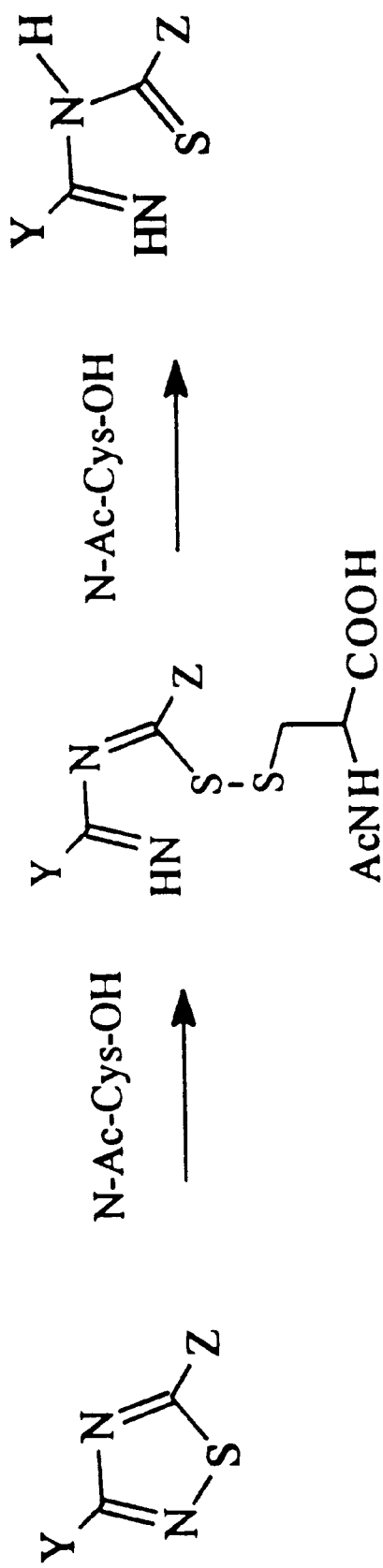
FIG. 1 is a diagrammatic representation of the chemical interaction between compounds (I) of the present invention and N-acetyl cysteine.

The reactivity of the compounds of the present invention towards cysteine activity dependent enzymes can be evaluated by their reactivity with N-acetyl cysteine. FIG. 1 illustrates the reaction between compounds of formula (I) of the present invention with N-acetyl cysteine. The first step forms a disulfide compound by cleavage of the S—N bond of the 1,2,4-thiadiazoles. The disulfide IX reacts with a second thiol to produce a compound of formula X.

The compounds of the present invention are those having amino acid or peptide residue side chains. The side chains can be attached at position C3 or C5 positions of 1,2,4-thiadiazole. The use of amino acid or peptide residues as side chains in the monocyclic compounds used in the present invention, particularly when they are attached to the nucleus at position 5, allows selection of an appropriate group having binding affinity for the enzyme which is to be inhibited by the compound. Furthermore, the binding affinity of the inhibitor can be tuned so that it binds to the enzyme at a close proximity of the active site cysteine residue with which it ultimately forms a dissulfide bond.

The presence of an appropriately chosen enzyme binding or recognition group as a side chain on the compound at a position remote from the —S—N=C— group allows the compound to seek out and bind to the selected enzyme, to enhance the chemical attack of the thiol group of the enzyme. Due to the presence of recognition side group, compounds of this nature, are highly selective in their attack upon a specific, chosen enzyme, and are much less reactive towards other thiols which they might encounter in a biological system.

Preferred compounds of formula (II) according to the invention are those in which A is glycyl, leucyl-prolyl and isoleucyl-prolyl; W is —$NH_2$ or —OH; and Y is lower alkyl (methyl), lower alkoxy (methoxy, n butoxy), lower aryl (phenyl), cinnamyl, 1-H-Indol-3-yl-methyl, —$CH_2$—$NR^3R^4$ where $R^3$ and $R^4$ are as previously defined, —$CH_2$—A—W where A and W are as previously defined.

Preferred compounds of formula (III) according to the invention are those in which A is leucyl, leucyl-prolyl or isoleucyl-prolyl and Z and Y are as defined above. Particularly preferred compounds of formula (III) are those in which Y is a lower alkoxy.

Preferred compounds of formula (IV) according to the invention are those in which A is phenyl alanyl, glycyl, $R_1$ is H and R is as previously defined.

The preferred compounds according to the present invention exhibit specificity to a particular cysteine activity dependent enzyme and thus are unreactive to other potential nucleophiles such as alcohols or amines.

As used herein:

The term "lower", as applied for example to lower alkyl, means 1 to 8 carbon atoms.

The term "aryl", alone or in combination, means a phenyl or naphthyl radical which optionally carries one or more substituents selected from alkyl, alkoxy, halogen, hydroxy, amino and the like, such as phenyl, p-tolyl, 4-methoxyphenyl, 4-(tert-butoxy)phenyl, 4-fluorophenyl, 4-chlorophenyl, 4-hydroxyphenyl, 1-naphthyl, 2-naphthyl and the like.

The term "arylalkoxy carbonyl", alone or in combination, means a radical of the formula —C(O)—O-arylalkyl, in which the term "arylalkyl" has the significance given above. An example of an arylalkoxy-carbonyl radical is benzyloxycarbonyl.

The term "arylalkyl" means an alkyl radical in which one hydrogen atom is replaced by an aryl radical, such as benzyl, phenylethyl and the like.

The term "arylalkenyl" means an alkenyl radical in which one hydrogen atom is replaced by an aryl radical such as 3-phenylallyl, 2-phenylallyl, 1-phenylallyl and the like.

The term "cycloalkylcarbonyl" means an acyl group derived from a monocyclic or bridged cycloalkanecarboxylic acid such as cyclopropanecarbonyl, cyclohexanecarbonyl, adamantanecarbonyl, and the like, or from a benz-fused monocyclic cycloalkanecarboxylic acid which is optionally substituted by, for example, alkylamino, such as 1,2,3,4-tetrahydro-2-naphthoyl, 2-acetamido-1,2,3, 4-tetrahydro-2-naphthoyl.

The term "arylalkanoyl" means an acyl radical derived from an aryl-substituted alkanecarboxylic acid such as phenylacetyl, 3-phenylpropionyl, hydrocinnamoyl, 4-phenlbutyryl, 2-naphthyl-acetyl, 4-chlorohydrocinnamoyl, 4-aminohydrocinnamoyl, 4-methoxyhydrocinnamoyl, and the like.

The term "aroyl" means an acyl radical derived from an aromatic carboxylic acid. Examples of such radicals include aromatic carboxylic acid, an optionally substituted benzoic or naphthoic acids such as benzoyl, 4-chlorobenzoyl, 4-carboxybenzoyl, 4-[(benzyloxy-carbonyl] benzoyl, 1-naphthoyl, 2-naphthoyl, 6-carboxy-2-naphthoyl, 6-[(benzyloxy)formamido]-2-naphthoyl, and the like.

The term "heterocyclyl", as used herein except where noted, represents a stable 5- to 7-membered mono or bicyclic or stable 7- to 10-membered bicyclic heterocyclic ring which is either saturated or unsaturated, and which consists of carbon atoms, and from one to three heteroatoms selected from the group consisting of N, O, S and wherein the nitrogen and sulfur heteroatoms may be optionally oxidized, and the nitrogen atom may optionally be quaternized, and including any bicyclic group in which any of the above defined heterocyclic rings is fused to a benzene ring. The heterocyclic ring may be attached at any heteroatom or carbon atom which results in the creation of a stable structure. Examples of such heterocyclic elements, commonly known as heterocyclyl include piperidinyl, piperazinyl, 2-oxopiperazinyl, 2-oxopiper-azinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolidinyl, isoxazolyl, isoxazolidinyl, morpholinyl, thiazolyl, thiazolidinyl, isothiazolyl, quinuclidinyl, isothiazoli-dinyl, indolyl, quinolinyl, isoquinolinyl, benzimidazolyl, thiadiazolyl, benzopyranyl, benzothiazolyl, benzoxazolyl, furyl, tetrahydrofuryl, tetrahydropyranyl, thienyl, benzothienyl, tetrahydroquinolinyl (e.g. 1,2,3,4-tetrahydro-2-quinolinyl, etc), 1,2,3,4-tetrahydro-isoquinolinyl (e.g. 1,2,3,4-tetrahydro-1-oxo-isoquinolinyl, etc.), quinoxalinyl, beta-carbolinyl, 2-benzofurancarbonyl, thiamorpholinyl, thiamorpholinyl sulfoxide, thiamorpholinyl sulfone, oxadiazolyl and the like. The heterocycle may be substituted on one or more carbon atoms or heteroatom which results in the creation of a stable structure.

"Amino acid residue" means any of the naturally occurring alpha-, beta-, and gamma-amino carboxylic acids, including their D and L optical isomers and racemic mixtures thereof, and the N-lower alkyl- and N-phenyl lower alkyl-derivatives of these amino acids. The amino acid residue is either bonded through a nitrogen of the amino acid or the carboxyl carbon of the amino acid. The naturally occurring amino acids which can be incorporated into the present invention include, but are not limited to, alanine, arginine, asparagine, aspartic acid, cysteine, cystine, glutamic acid, glutamine, glycine, histidine, isoleucine, leucine, lysine, methionine, ornithine, phenylalanine, proline, serine, threonine, thyroxine, tryptophan, tyrosine, valine, beta-alanine, and gamma-aminobutyric acid. Preferred amino acid residues include proline, lysine, leucine, phenylalanine, tyrosine, isoleucine, alanine, gamma-amino butyric acid, valine, glycine and phenlyglycine.

"Amino acid residues" further includes commonly known synthetic unnatural amino acids and any logically designed peptidomimetic in which the H-bonding elements of the amino acid residue is taken into consideration. Synthetic unnatural amino acids include amino acids such as 4-hydroxyproline, O-benzylthreonine, 4-cyclohexylproline, 3,4,5-trimethyl proline, 3,4-dimethylproline, 4,5-dimethylproline, 4-chlorophenylalanine, octahyro-indole-2-carboxylic acid, octahydro-isoquinoline-3-carboxylic acid, piperidinyl-2-carboxylic acid, piperazinyl-2-carboxylic acid, 4-phenylproline, 3-phenylproline, 4 cyclohexylproline, 3-cyclohexylproline, 4-aminoproline, octahydro-cyclopentane[b]pyrrole-2-carboxylic acid, statone, statine, norstatine derivatives, 4-amino-3-hydroxy-5-phenyl-pentanoic acid, 4-amino-3-oxo-5-phenyl-pentoic acid, 3-amino-2-hydroxy-4-phenylbutanoic acid, 2,2-difluorostatine, cyclohexylalanine, and the following amino acids:

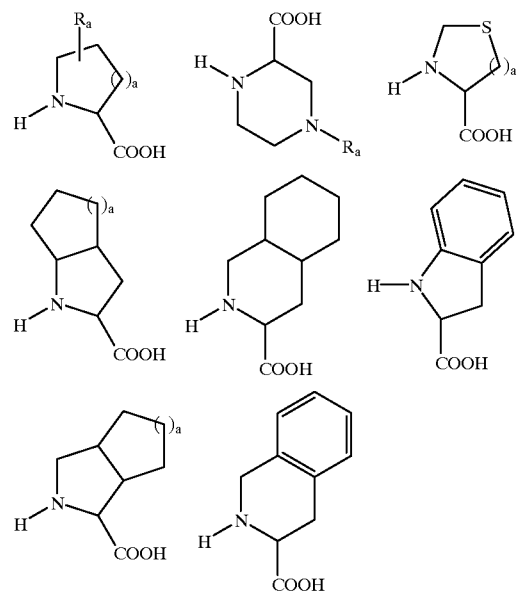

wherein a stands for 1 or 2. $R_a$ stands for hydrogen, alkyl, hydroxy, alkoxycarbonylamino.

Representative examples of logically designed peptidomimetics are illustrated below:

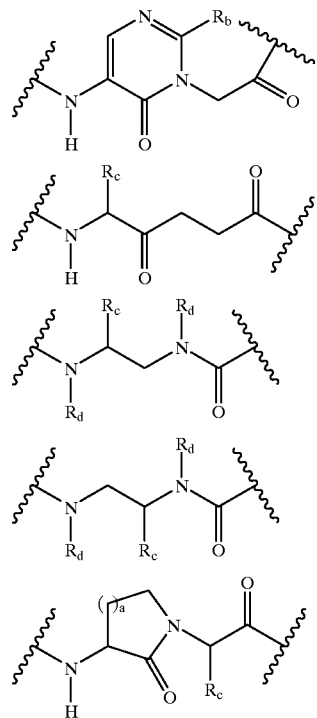

-continued

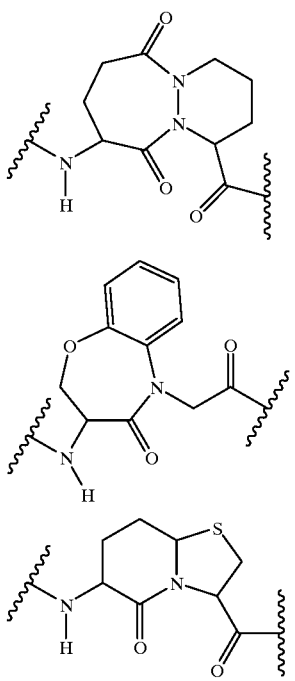

where $R_b$, $R_c$ and $R_d$ independently represents hydrogen, and an alkyl.

All alpha-amino acids except glycine contain at least one asymmetric carbon atom. As a result, they are optically active, existing in either D or L form or as a racemic mixture. Accordingly, some of the compounds of the present invention may be prepared in optically active form, or as racemic mixtures of the compounds claimed herein.

A peptide residue contains a peptide bond which may be formed between the carbonyl function of an amino acid and another amino compound which may be another amino acid or an amine. Compound of the present invention may be in isosteric form e.g., —CH₂NH— (reduced), —COCH₂— (keto), —CH(OH)(CH₂— (hydroxy), —CH(NH₂)CH₂— (amino), —CH₂CH₂— or —CH₂CH₂CH₂— (hydrocarbon). Preferably a compound of the present invention has no peptidic carbamoyl in isosteric form. When it has peptidic carbamoyl groups in isosteric form, it has one or two, preferably one peptidic bond in isosteric form.

A peptide residue consists of amino acid residues, preferably in their natural configuration. When there are amino acids in unnatural configuration there preferably is only one such amino acid in unnatural configuration. Amino acid residue as used herein includes amino acid residues such as octahydroindole-2-carboxylic acid and hydroxyproline.

The term "R", when referred as an "N-protecting group", is an amino protecting group. Examples of protecting groups as R are for example disclosed in "Protective Groups in Organic Synthesis", T. V. Greene, J. Wiley & Sons NY (1981)0 219–287. These include but are not limited to acyl such as acetyl, methoxysuccinyl, hydroxysuccinyl or benzoyl optionally substituted on the phenyl ring with for example p-methoxycarbonyl, p-methoxy or p-nitro; alkoxycarbonyl such as t-butyloxycarbonyl; arylmethoxycarbonyl such as 9-fluorenylmethoxycarbonyl or benzyloxy carbonyl optionally substituted on the phenyl ring with p-methoxy, p-nitro, p-chloro or m-phenyl; arylmethyl such as benzyl optionally substituted on the aromatic ring with p-methoxy, p-nitro or p-chloro; or arylsulfonyl such as phenylsulfonyl optionally substituted with p-methyl or p-methoxyl or naphthylsulfonyl optionally substituted on the aromatic ring with example amino or dialkylamino.

The term "aryloxyalkanoyl" means an acyl radical of the formula aryl-O-alkanoyl and the term "heterocyclyloxycarbonyl" means an acyl group derived from heterocyclyl-O—CO— wherein heterocyclyl is defined above.

The term "heterocyclylalkanoyl" means an acyl radial derived from a heterocyclyl-substituted alkane carboxylic acid wherein heterocyclyl has the same meaning given above.

The term "heterocyclyalkoxycarbonyl" means an acyl radical derived from a heterocyclyl-substituted alkyl-O—CO wherein heterocyclyl has the same significance given above.

The term "aminoalkanoyl" means an acyl radical derived from an amino-substituted alkanecarboxylic acid wherein the amino group can be a primary, secondary or tertiary amino group containing substituents selected from hydrogen, and alkyl, aryl, arylalkyl, cycloalkyl, cycloalkylalkyl radicals and the like.

"Optional" or "optionally" means that the subsequently described event or circumstances may or may not occur, and that the description includes instances where the said event or circumstance occurs and instances in which it does not. For example, "phenyl . . . optionally substituted" means that the phenyl may or may not be substituted and that the description includes both unsubstituted phenyl and phenyl wherein there is substitution.

Certain of the compounds of the invention have chiral centers and exist as optical antipodes. The invention described and claimed herein includes each of the individual enantiomers as well as their racemic modifications and the racemic mixture.

"Pharmaceutically acceptable, non-toxic salts" refers to pharmaceutically acceptable salts of the compounds of this invention which retain the biological activity of the parent compounds and are not biologically or otherwise undesirable (e.g. the salts are stable). Salts of the two types may be formed from the compounds of this invention: (1) Salts of inorganic and organic bases from compounds of formulae I, II, III and IV which have a carboxylic acid functional group and (2) Acid addition salts may be formed at the amine functional group of many of the compounds of this invention.

Pharmaceutically acceptable salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Pharmaceutically acceptable, non-toxic salts derived from organic bases include salts of primary, secondary and tertiary amines, substituted amines including naturally occurring substituted amines, cyclic amines and basic ion exchange resins. Such salts are exemplified by, for example isopropopylamine, trimethyl-amine, diethylamine, triethylamine, tripropylamine, ethanolamine, 2-dimethylaminoethanol, tromethamine, dicyclohexamine, lysine, arginine, histidine, caffeine, procaine, hydrabramine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, piperidine, tromethamine, dicyclohexylamine, choline and caffeine.

Pharmaceutically acceptable acid addition salts are formed with inorganic acids such as halo acids, sulfuric acid, nitric acid, phosphoric acid and the like and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The term "animals" refers to humans as well as all other animal species, particularly mammals (e.g. dogs, cats, horses, cattle, pigs, etc.), reptiles, fish, insects and helminths.

The specific, most preferred compounds according to the present invention are the following:

2-(3-methoxy-[1,2,4]thiadiazol-5-ylamino)-acetamide
2-(3-n-Butoxy-[1,2,4]thiadiazol-5-ylamino)-acetamide
2-[3-(3-Phenylallyl)-[1,2,4]thiadiazol-5-ylamino]-acetamide
2-[3-(1H-Indol-3-ylmethyl)-[1,2,4]thiadiazol-5-ylamino]-acetamide
N-(3-methoxy-[1,2,4]thiadiazol-5-yl)-L-leucyl-L-proline
N-(3-Butoxy-[1,2,4]thiadiazol-5-yl)-L-leucyl-L-proline
N-(3-Phenyl-[1,2,4]thiadiazol-5-yl)-L-leucyl-L-proline
N-(3-Methyl-[1,2,4]thiadiazol-5-yl)-L-leucyl-L-proline
N-(3-methoxy-[1,2,4]thiadiazol-5-yl)-L-isoleucyl-L-proline
N,N'-{3-methylene-[1,2,4]thiadiazol-5-yl}-di-{L-leucyl-L-proline methyl ester},
which has the following chemical formula:

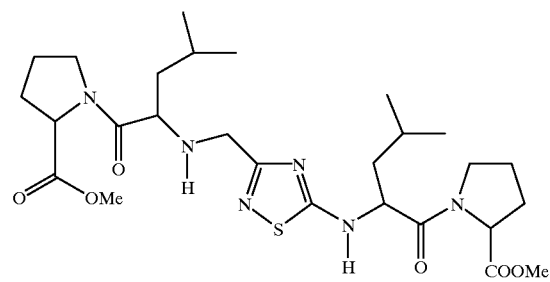

{3-[4-(2-pyridyl)piperazinylmethyl]-1,2,4-thiadiazol-5-yl}-leucyl-proline, which has the following chemical formula:

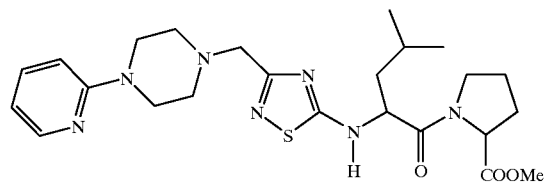

5-{3-methoxy-1,2,4-thiadiazolyl}carbamoyl-leucyl isoamylamide

5-{3-methoxy-1,2,4-thiadiazolyl}carbamoyl-isoleucyl isoamylamide

{3-methoxy-[1,2,4]-thiadiazol-5-yl}carbamoyl-L-leucyl-L-proline.

3-methoxy-5-carbobenzyloxy-phenylalaninamido-[1,2,4]-thiadiazole.

3,5-di-(N-carbobenzyloxy-L-phenylalaninamido)-[1,2,4] thiadiazole, which has the following chemical formula:

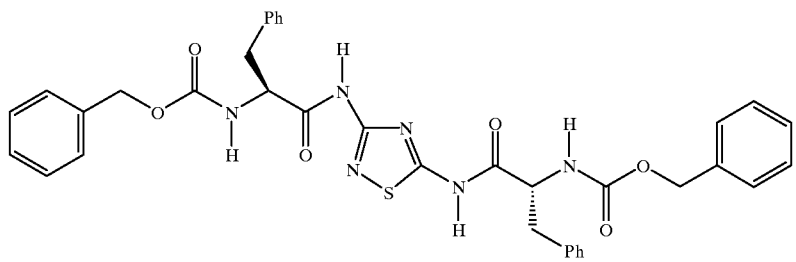

The present invention provides synthetic methods for preparing compounds according to the invention. The choice of method depends largely upon the selected Z and Y group that is the substituent on C3 and C5 positions in the final compound.

The compounds of formula II are prepared by reaction of a compound of formula 3 with a primary or secondary amine. Examples of those amines are 2-pyridylpiperazine and leucyl-proline methyl ester. This method is appropriate for compounds in which Y is lower alkyl, lower alkoxy, heterocyclyl, 1-haloalkyl, aryl, dialkylamino:

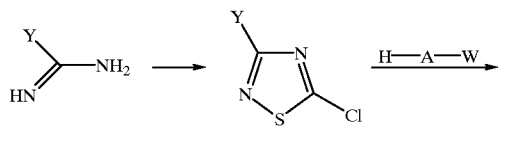

The reaction is normally carried out in an inert solvent such as N,N-dimethylformamide, tetrahydrofuran, dichloromethane, acetonitrile, dimethylsulfoxide in the presence or absence of a base such as 1 to 3 mole of triethylamine per mole of compound 3. These solvents may be used singularly or in combination of any ratio as necessary. Reaction temperature can be chosen over the range of from 0° C. to 150° C., being preferably about 10 to 65° C. Reaction time is normally about 1 to 50 hours, preferably 1 to 8 hours. The amount of amine used is 1 to 3 mole per mole of compound 3.

The compounds of formula 3 can be produced by treating the corresponding amidine derivative with perchloromethyl mercaptan in a two phase mixture of dichloromethane and sodium hydroxide at 0 to 25° C. for 2 to 6 hours.

Preparative methods for compound 1 include those reported in U.S. Pat. No. 3,324,141; J. Org. Chem., 1962, 27, 2589; Chem. Ber., 1957, 90, 182.

Compounds of formula III wherein the spacer X is —NH—CO—CH$_2$ are prepared by N-alkylating a compound of formula (4) with an amine:

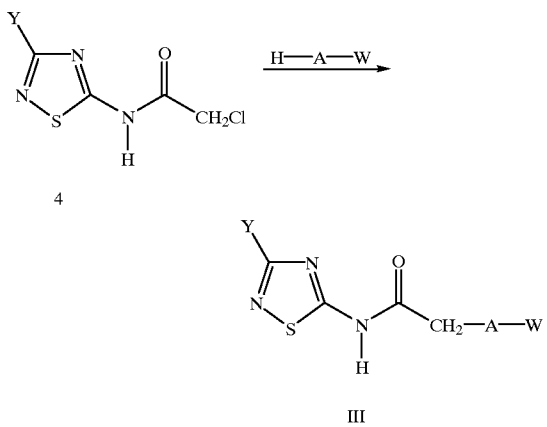

The compounds are isolated by conventional means. Compounds (4) are in turn prepared by reacting compound (5) with bromoacetyl bromide in an inert solvent such as methylene chloride or tetrahydrofuran in the presence of a base such as triethylamine. Compounds (5) are prepared from the amidine (1) with potassium thiocyanate (KSCN) in the presence of base such as sodium hydroxide in an inert solvent such acetone and water.

Compounds of formula III in which the spacer X is —NH—CO— are prepared by reaction of a compound (5) with H—A—W in the presence of 1,1-carbonyl diimidazole in an inert solvent such as THF or DMF.

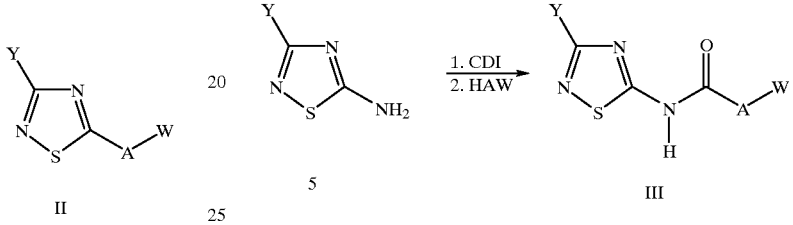

The compounds of formula (IV) are produced by peptide coupling between compound (5) with N-protected amino acid or N-protected peptide carboxylic acid R—A—OH using conventional peptide coupling reagent such as 1,1-carbonyl di-imidazole or diphenylphosphoryl azide in an inert solvent such as dimethylformamide or tetrahydrofuran:

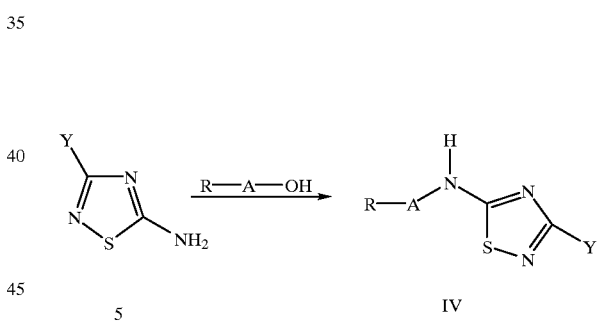

The compounds R—A—OH are generally commercially available from Sigma-Aldrich Inc., for example, carbobenzyloxy-L-phenylalanine, carbobenzyloxy-L-phenylalanyl-L-alanine (R—A'—OH as a N-protected amino acid), N-t-Boc-3-amino-2-hydroxy-5-methyl-hexanoic acid (R—A'—OH as a protected dipeptide with the peptide bond in carbamoyl form), N-t-Boc-3-amino-2-hydroxy-4-phenylbutyric acid (R—A'—OH as a N-protected peptide in isosteric form). If not commercially available such compounds can be prepared according to the method disclosed in Synthetic Peptides, vol. 1 by George R. Pettit, Van Nostrand Reinhold, 1970.

In an alternative route for the preparation of compounds of formula (IVA) within the scope of this invention, a compound of formula (6) is reacted with N-protected amino acid or peptide acid R—A—OH using conventional peptide coupling reagent such as 1,1-carbonyl di-imidazole or diphenylphosphoryl azide in an inert solvent such as dimethylformamide or tetrahydrofuran.

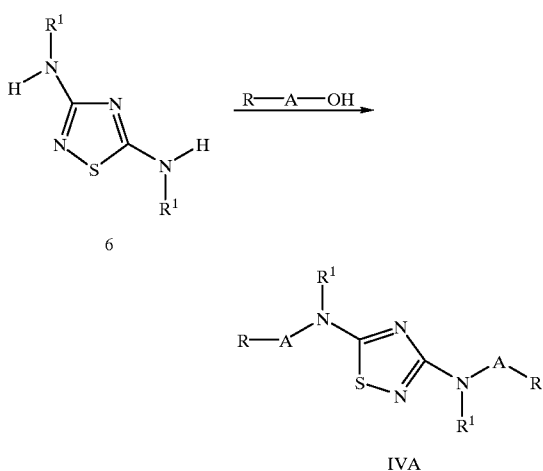

6

R—A—OH →

IVA

The preparation of pseudopeptides within the scope of the present invention involves the use of the bis-chloro derivative 7 as a starting material. The amines H—A—W reacts with compound 7 in the presence of a phase transfer catalyst such as tetra-N-butylammonium bromide in an inert solvent such as dimethylformamide at room temperature over a period of 20 to 30 hours to give compound 8. This reaction is temperature dependent. At elevated temperature, preferably 70–90° C., the disubstituted product compound $II_A$ is formed. Compound 8 also reacts with other amines such as H—A—W or $R^3R^4NH$ to give the compounds of formula $II_A$ and $II_B$ respectively.

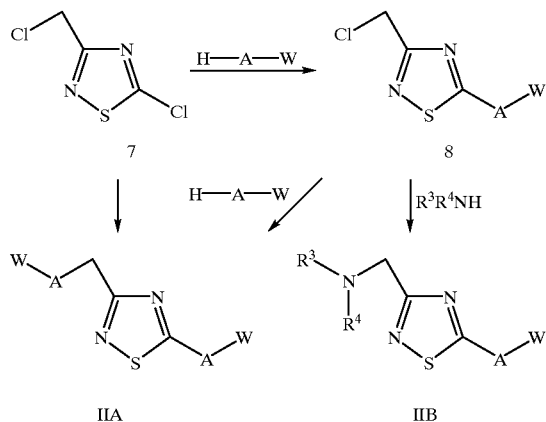

Certain compounds of this invention may be converted to their corresponding pharmaceutically acceptable acid addition salts by virtue of the presence of a basic amine nitrogen. These compounds may be converted from the free base form to various acid addition salts by treating with a stoichiometric excess of the appropriate organic or inorganic acid, such as, for example, phosphoric, pyruvic, hydrochloric or sulfuric acid and the like. Typically, the free base is dissolved in a polar organic solvent such as p-dioxane or dimethoxyethane, and the acid added thereto. The temperature is maintained between 0° C. and 50° C. The resulting acid addition salt precipitates spontaneously or may be precipitated out of solution with a less polar solvent. These acid addition salts may be decomposed to the corresponding free base by treating with a stoichiometric amount of a suitable base, such as potassium carbonate or sodium hydroxide, typically in the presence of aqueous solvent, and at a temperature of between about 0° C. and 50°. The free base form is isolated by conventional means, such as extraction with an organic solvent. Acid addition salts of the compounds of the present invention may be interchanged by taking advantage of differential solubilities of the salts, volatilities or acidities of the acids, or by treating with an appropriately loaded ion exchange resin. For example, the interchange is effected by the reaction of a salt of the compounds of formula I with a slight stoichiometric excess of an acid of a lower pKa than the acid component of the starting salt. This is carried out at a temperature between about 0° C. and the boiling point of the solvent being used.

For the treatment of diseases and/or disorders herein above referred to, the compounds of the present invention may be used orally, or parenterally in formulations containing conventional non-toxic pharmaceutically acceptable carriers, adjuvants and vehicles. The term parenteral as used herein includes subcutaneous injection or infusion techniques. In addition to the treatment of warm-blooded animals such as mice, rats, horses, cattle, sheep, dogs, cats, etc., the compounds of the invention are effective in the treatment of humans.

For compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as liquid pharmaceutically administrable compositions can, for example, be prepared by mixing, dissolving, dispersing, etc. the active compounds as defined above the optional pharmaceutically adjuvants in a carrier, such as, for example, water, saline, aqueous dextrose, glycerol, ethanol, and the like, to hereby form a solution or suspension. If desired, the pharmaceutical composition to be administered may also contain a minor amount of non-toxic auxiliary substances such as wetting or emulsifying agents and the like, for example, sodium acetate, sorbitan monolaurate, triethanolamine sodium acetate, triethanolamine oleate, etc. Actual methods of preparing such dosage forms are known, or will be apparent to those skilled in this art: for example, see Remington's Pharmaceutical Sciences, Mack Publishing Company, Easton, Pa., 15th Edition, 1975. The composition of formulation to be administered will, in any event, contain a quantity of the active compounds in an amount effective to alleviate the symptoms of the subject being treated.

The pharmaceutical compositions containing the active ingredient may be in a form suitable for oral use, for example, as tablets, troches, lozenges, aqueous or oily suspensions, dispersible powders or granules, emulsions, hard and soft capsules, or syrups or elixirs. Compositions intended for oral use may be prepared according to any method known to the art for the manufacture of pharmaceutical compositions and such compositions contain one or more agents from the group consisting of sweetening agents, flavouring agents, colouring agents and preserving agents in order to provide pharmaceutically elegant and palatable preparations.

Tablets contain the active ingredient in admixture with the non-toxic pharmaceutically acceptable excipients which are suitable for the manufacture of tablets. The excipients may be for example, inert diluents, such as calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be coated by known techniques to delay the disintegration and absorption in the gastrointestinal tract and thereby provide a sustained action over long period.

Formulations for oral use may also be presented as had gelatin capsules wherein the active ingredients are mixed with inert solid diluent, for example, calcium phosphate or kaolin, or as soft gelating capsules wherein the active ingredient is mixed with water or an oil medium, for example peanut oil, liquid paraffin, or olive oil.

Aqueous suspensions contain the active materials in admixture with the excipient suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum and gum acacia; dispersing or wetting agents may be a naturally-occurring phosphate, for example lecithin, or condensation products of an alkene oxide with fatty acids, for example polyoxyethylene stearate, or condensation products of ethylene oxide with long chain aliphatic alcohols, for example heptadecathyl-eneoxycetanol, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, P-hydroxy-benzoate, one or more colouring agents, such as sucrose or saccharin. Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbio acid.

Dispersible powders and granules suitable for preparation of an aqueous suspension by the addition of water provide the active ingredient in admixture with the dispersing or wetting agent, suspending agent and one or more preservatives. Suitable dispersing or wetting agents and suspending agents are exemplified by those already mentioned above. Additional recipients, for example sweetening, flavouring and colouring agents, may also be present.

The pharmaceutical composition of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring phosphates, esters derived from fatty acids and hexitol anhydrides, for example sorbitan monooleate, and condensation products of the said partial ester with ethylene oxide, for example polyoxyethylene sorbitan monooleate. The emulsion may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solutions and isotonic sodium chloride solution. In addition, fixed oils are conventionally employed as a solvent or suspending medium. For this purpose any bland fixed oil may be employed including synthetic mono- or diglycerides. In addition, fatty acids such as oleic acid find use in the preparation of injectables.

Parenteral administration is generally characterized by injection, either subcutaneously, intramuscularly or intravenously. Injectables can be prepared in conventional forms, either as liquid solutions or suspension in liquid prior to injection, or as emulsions. Suitable excipients are for example, water, saline, dextrose, glycerol, ethanol or the like. In addition, if desired, the pharmaceutical compositions to be administered may also contain minor amounts of non-toxic auxiliary substance such as wetting or emulsifying agents, pH buffering agents and the like, such as for example, sodium acetate, sorbitan monolaurate, triethanolamine oleate, etc.

The amount of active ingredient that may be combined with the carrier materials to produce a single dosage form will vary depending upon the host treated and the particular mode of administration of humans may contain from 0.5 mg to 5 mg of active agent compounded with an appropriate and convent amount of carrier material which may vary from about 5 to about 95% of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, drug combination and the severity of the particular disease undergoing therapy.

The invention is further described and illustrated in the following specific examples.

EXAMPLE 1

A. Preparation of Amidines, compounds of formula I.

Selected amidines were from commercial sources (Aldrich and/or Lancaster). Those which were not commercially available were prepared according to published procedures. [Sandler, S. R. and Karo, W. in Organic Functional Group Preparations, 2nd Ed., Academic Press, Inc., Toronto, Volume II, Chapter 7, 1986 and Volume III, Chapter 6, 1989 and references cited therein; MacLeod, A. M. et al. in J. Med. Chem. 1990, 33, 2052–2059].

B. Preparation of 2-(3-Chlorophenyl)-2-(tetrahydropyran-2-yloxy)acetamidine hydrochloride.

To a solution of sodium bisulfite (27.66 g, 0.266 mol) in water (120 mL) was added 3-chlorobenzaldehyde (25.0 g, 0.178 mol). After stirring for 20 min, a solution of sodium cyanide (12.4 g, 0.2525 mol) in water (80 mL) was added dropwise. Ethyl acetate (50 mL) was added and the resulting mixture was stirred for another 3 h. The organic layer was collected, washed with brine, dried (sodium sulfate), filtered and evaporated to dryness. The residue was dissolved in dichloromethane (200 mL) and cooled in ice. Dihydropyran (20.62 g, 0.2451 mol) and pyridinium p-toluene sulfonate (6.5 g, 25.9 mmol) were then added successively and the mixture was stirred at room temperature for 16 h. The organic layer was successively washed with water (50 mL), 5% sodium bisulfite solution (2×50 mL) and brine (50 mL). The organic fraction was dried (sodium sulfate), filtered and evaporated to give an oil. Purification by column chromatography on silica gel using a mixture of hexane and ethyl acetate (95/5) as eluant afforded 31.5 g (70%) of 2-(3-chlorophenyl)-2-[(tetrahydropyran-2-yloxy)]acetonitrile (mixture of diastereoisomers) as a clear oil which was contaminated with <5% of 3-chlorobenzaldehyde. $^1$H-NMR (CDCl$_3$) δ7.30–7.60 (m, 4H, Ar-H), 5.59 (s, 0.3H, αH) and 5.41 (s, 0.7H, αH), 5.12 (t, J=2.9 Hz, 0.3H, OCHO) and 4.77 (t, J=2.9 Hz, 0.7H, OCHO), 3.60–4.05 (m, 2H, CH$_2$O), 1.50–2.06 (m, 6H, 3 CH$_2$). Small pieces of sodium (192 mg, 7.9 mmol) was added to anhydrous ethanol (200 mL) under a positive pressure of nitrogen at room temperature. After all the sodium had dissolved, 2-(3-chlorophenyl)-2-[(tetrahydropyran-2-yloxy)]acetonitrile (19.54 g, 77.6 mmol) was added neat and the contents of the flask was rinsed with ethanol (20 mL) and added to the reaction mixture. The progress of the reaction can be monitored by TLC using a mixture of hexane and ethyl acetate (1/1) as solvent system. After stirring for 16 h, the reaction mixture was cooled to ca. –40° C. (dry ice-methanol-water) and an ethanolic solution of ammonia (77.6 mL of a 2M solution, 0.1552 mol) was quickly added followed by solid ammonium chloride (4.02 g, 75.15 mmol). The reaction mixture was allowed to warm to room temperature overnight. The reaction mixture was filtered over a pad of celite. The filtrate was collected and evaporated to dryness and then pumped under high vacuum to afford 2-(3-chlorophenyl)-2-(tetrahydropyran-2-yloxy)acetamidine hydrochloride (23 g) as a white foam in almost quantitative yield. $^1$H-NMR (CDCl$_3$) δ9.00–9.80 (br., 1H, NH), 8.00–8.80 (br., 1H, NH), 7.30–7.64 (m, 3H, Ar-H), 5.85 (s, 0.4H, αH) and 5.75 (s, 0.6H, αH), 4.84 (t, J=3.3 Hz, 0.4H, OCHO) and 4.57 (t, J=3.3 Hz, 0.6H, OCHO), 3.41–3.83 (m, 2H, CH$_2$O), 2.20–2.60 (br., 1H, NH), 1.46–1.86 (m, 6H, 3 CH$_2$).

C. In a similar manner, 2-pyridyl-2-(tetrahydropyran-2-yloxy)acetamidine hydrochloride salt was prepared as an orange foam (crude yield 96.0%). $^1$H-NMR (CDCl$_3$) δ9.00–9.80 (br., 1H, NH), 8.00–8.80 (br., 1H, NH), 8.56–8.61 (d, J=4.4 Hz, 1H, Py-H), 7.28–7.84 (m, 3H), 5.75 (s, 0.4H, αH) and 5.67 (s, 0.6H, αH), 4.93 (t, J=2.5 Hz, 0.4H, OCHO) and 4.71 (t, J=2.5 Hz, 0.6H, OCHO), 3.49–3.93 (m, 2H, CH$_2$O), 1.53–1.92 (m, 6H, 3 CH$_2$).

EXAMPLE 2

A. Preparation of 5-Chloro-3-methoxy-[1,2,4]thiadiazole.

To an ice-cooled mixture of O-methylisourea hydrochloride (11.06 g, 0.1 mol) in chloroform (150 mL) was added a solution of perchloromethyl mercaptan (11.0 mL, 0.1 mol) in chloroform (50 mL) dropwise over a period of 45 min. Then, a cold solution of sodium hydroxide (16 g, 0.4 mol in 30 ml water) was added dropwise while maintaining the reaction temperature to <5° C. The progress of the reaction was monitored by TLC using a mixture of hexane and ethyl acetate (9/1) as eluent. After 3 h at room temperature, the organic layer was collected, dried (sodium sulfate), filtered and then concentrated in vacuo. Purification by column chromatography on silica gel using a solvent gradient of a mixture of hexane and ethyl acetate (100/0, 95/5 then 9/1) afforded 5-chloro-3-methoxy-[1,2,4]thiadiazole (6.01 g, 39.9%) as a light yellow oil. $^1$H-NMR (CDCl$_3$) δ4.02 (s, OMe, 3H); $^{13}$C-NMR (CDCl$_3$) d 173.56 (C3), 169.68 (C5), 57.07 (OMe); MS (APCl) m/z 151.1 (M$^+$+1), 108.0, 94.0, 73.0, 58.0.

B. In a similar fashion, the following compounds were prepared:

3-Butoxy-5-chloro-[1,2,4]thiadiazole, light yellow oil, yield (50.9%). $^1$H-NMR (CDCl$_3$) δ4.35 (t, J=6.6 Hz, 2H, CH$_2$), 1.75 (m, 2H, CH$_2$), 1.44 (m, 2H, CH$_2$), 0.93 (t, J=7.1 Hz, 3H, CH$_3$); $^{13}$C-NMR (CDCl$_3$) δ173.27 (C3), 169.37 (C5), 70.17 (C1'), 30.70 (C2'), 18.96 (C3'), 13.67 (C4').

N-(5-Chloro-[1,2,4]thiadiazol-3-yl)-acetamide or 3-acetamido-5-chloro-1,2,4-thiadiazole, light yellow solid on standing, yield (34.8%). $^1$H-NMR (CDCl$_3$) δ2.50 (s, Me); $^{13}$C-NMR (CDCl$_3$) δ173.97 (C3), 171.86 (CO), 164.07 (C5), 22.54 (CH$_3$).

3-(5-Chloro-[1,2,4]thiadiazol-3-ylmethyl)-1H-indole or 5-chloro-3-{1H-indol-3-yl-methyl}-1,2,4-thiadiazole, light brown solid, yield (28%). $^1$H-NMR (CDCl$_3$) δ8.29 (br. s, 1H, NH), 7.68 (d, J=7.8 Hz, 1H, CHNH), 7.11–7.33 (m, 4H, Ar-H), 4.48 (s, 2H, CH$_2$); $^{13}$C-NMR (CDCl$_3$) δ175.50 (C3), 173.00 (C5), 136.31, 127.13, 123.19, 122.26, 119.70, 119.05, 111.41, 110.55, 29.97 (CH$_2$); MS m/z 249.7 (M$^+$), 130.1, 117.1.

EXAMPLE 3

A. Preparation of 5-Chloro-3-[3-chlorophenyl-1-(tetrahydropyran-2-yloxy)methyl]-[1,2,4]thiadiazole.

To an ice-cooled solution of 2-(3-chlorophenyl)-2-(tetrahydropyran-2-yloxy)acetamidine hydrochloride (12.0 g, 39.51 mmol) in dichloromethane (20 mL) and sodium hydroxide (9.49 g, 0.237 mol, dissolved in 60 mL water) was added a solution of perchloromethyl mercaptan (9.18 g, 49.46 mmol) in dichloromethane (50 mL) over a period of 35 min. The reaction mixture was stirred at ice-cold temperature for a further 1 h and the organic layer was collected, dried (sodium sulfate), filtered and concentrated in vacuo. Purification by column chromatography on silica gel using a mixture of hexane and ethyl acetate (94/6) afforded the title compound as a light yellow oil (8.4 g, 61.5%). $^1$H-NMR (CDCl$_3$) δ7.56 (d, J=6.9 Hz, 1H, Ar-H), 7.39–7.44 (m, 1H, Ar-H), 7.28–7.32 (m, 2H, Ar-H), 6.08 and 6.03 (s, 0.5H each, α-H), 4.84 and 4.72 (t, J=3.1 Hz, 0.5H each, OCHO), 3.49–3.92 (m, 2H, OCH$_2$), 1.55–1.94 (m, 6H, 3CH$_2$).

B. In a similar manner, the following compounds were prepared:

5 3-[(5-Chloro-[1,2,4]thiadiazol-3-yl)-(tetrahydropyran-2-yloxy)methyl]-pyridine, brown oil, 28.7% yield (mixture of diastereoisomers). $^1$H-NMR (CDCl$_3$) δ8.55 and 8.52 (d, J=4.5 Hz, 0.67 and 0.33 H each), 7.69–7.81 (m, 2H), 7.18–7.28 (m, 1H), 6.20 and 6.15 (s, 0.33 and 0.67 H each, ArCHO), 4.81–4.87 (m, 1H, OCHO), 3.84–3.90 (m, 1H, OCH), 3.44–3.54 (m, 1H, OCH), 1.90–1.96 (m, 1H), 1.75–1.80 (m, 2H), 1.51–1.60 (m, 3H); MS m/z 312.1 (M$^+$+1), 228, 210, 85. 5-Chloro-3-chloromethyl-[1,2,4]thiadiazole, brown oil, 83.6% yield. $^1$H-NMR (CDCl$_3$) δ4.70 (s); $^{13}$C-NMR (CDCl$_3$) δ174.33 (C3),170.56 (C5), 40.17 (CH$_2$).

EXAMPLE 4

Preparation of 2-(3-methoxy-[1,2,4]thiadiazol-5-ylamino)-acetamide.

To a suspension of glycinamide hydrochloride (0.55 g, 5 mmol) in DMF (10 mL) was added triethylamine (1.7 mL, 12 mmol) and the resulting mixture was stirred for 15 min at room temperature. This was added to a solution of 5-chloro-3-methoxy-[1,2,4]thiadiazole (0.38 g, 2.5 mmol, prepared according to the procedure by Goerdeler, J. et al. in Chem. Ber. 1955, 88, 843) in DMF (15 mL). Then, tetra-butylammonium bromide (50 mg) was added and the resulting suspension was heated at 80–85° C. for 1.5 h. On cooling to room temperature, the reaction mixture was diluted with water and ethyl acetate. The organic layer was collected, washed with brine, sat. Sodium bicarbonate solution, brine, dried (sodium sulfate), filtered and concentrated in vacuo. Purification by column chromatography on silica gel using a solvent mixture of dichloromethane and methanol (95/5 and 9/1) afforded 2-(3-methoxy-[1,2,4]thiadiazol-5-ylamino)-acetamide (75 mg, 16%) as a white solid. $^1$H-NMR (MeOD) δ4.03 (s, 2H, NCH2), 3.94 (s, 3H, OMe); $^{13}$C-NMR (MeOD) δ182.0, 173.3, 170.0, 56.7 (MeO), 47.9; MS (m/z) 189 (M$^+$+1), 172, 144, 87.

EXAMPLE 5

A. Preparation of (3-methoxy-[1,2,4]thiadiazol-5-ylamino)-acetic acid methyl ester or N-{3-methoxy-[1,2,4]-thiadiazol-5-yl}-glycine methyl ester.

In a similar manner as described in example 4, a suspension of glycine methyl ester hydrochloride (0.63 g, 5 mmol) in DMF (10 mL) was added triethylamine (1.7 mL, 12 mmol) and the resulting mixture was stirred for 15 min at room temperature. This was added to a solution of 5-chloro-3-methoxy-[1,2,4]thiadiazole (0.38 g, 2.5 mmol) in DMF (15 mL). Then, tetrabutylammonium bromide (50 mg) was added and the resulting suspension was heated at 80–85° C. for 1.5 h. On cooling to room temperature, the reaction mixture was worked up as usual and the product was purified by column chromatography on silica gel using a solvent mixture of hexane and ethyl acetate (6/4) thereby affording (3-methoxy-[1,2,4]thiadiazol-5-ylamino)-acetic acid methyl ester (310 mg, 60.1%) as a white solid. $^1$H-NMR (CDCl$_3$) δ7.20 (br.s, 1H, NH), 4.12 (br. s, 2H, NCH$_2$), 3.91 (s, 3H, OMe), 3.74 (s, 3H, OMe); $^{13}$C-NMR (CDCl$_3$) d 182.5 (C3), 170.0 (C=O), 168.1 (C5), 56.2 (OMe), 52.6 (OMe), 46.1 (CH$_2$).

B. Proceeding in a similar manner as described in example 5A, the following compounds were prepared:

(3-n-Butoxy-[1,2,4]thiadiazol-5-ylamino)-acetic acid methyl ester or N-{3-n-butoxy-[1,2,4]-thiadiazol-5-yl}-glycine methyl ester, off-white solid on standing, 65% yield. $^1$H-NMR (CDCl$_3$) δ6.98 (br. s,1H, NH), 4.29 (t, J=5.0 Hz, 2H, OCH$_2$), 4.18 (br. s, 2H, NCH$_2$), 3.80 (s, 3H, OMe), 1.75 (m, 2H, OCH$_2$ CH$_2$), 1.46 (m, 2H, CH$_2$ CH$_3$), 0.94 (t, J=7.1 Hz, 3H, CH$_3$); $^{13}$C-NMR (CDCl$_3$) δ182.1 (C3), 170.0 (C=O), 167.8 (C5), 69.0 (OCH$_2$), 52.7 (OMe), 46.1 (NCH$_2$), 30.9, 19.0, 13.7.

[3-(3-Phenyl-allyl)-[1,2,4]thiadiazol-5-ylamino]-acetic acid methyl ester or N-{3-cinnamyl-[1,2,4]-thiadiazol-5-yl}-glycine methyl ester; off-white solid, 68% yield. $^1$H-NMR (CDCl$_3$) δ7.18–7.40 (m, 6H, Ar-H and NH), 6.42–6.55 (m, 2H, HC=CH), 4.12 (br. s, 2H, NCH), 3.75 (s, 3H, OMe), 3.66 (d, J=6.0 Hz, 2H, C=CCH$_2$); $^{13}$C-NMR (CDCl$_3$) δ183.6 (C3), 172.0 (C5), 170.0 (C=O), 137.2, 132.3, 128.5 (C-ortho), 127.3, 126.3 (C-meta), 125.2, 52.6 (OMe), 46.7 (NCH$_2$), 36.8 (C=CCH$_2$).

[3-(1H-Indol-3-ylmethyl)-[1,2,4]thiadiazol-5-ylamino]-acetic acid methyl ester or N-{3-(1H-Indol-3-ylmethyl)-[1,2,4]-thiadiazol-5-yl}-glycine methyl ester; light brown solid, 71.4% yield. $^1$H-NMR (CDCl$_3$) d (rotamers) 8.36 (br. s,1H, NH), 7.72 and 7.64 (d, J=7.7 Hz, 0.25H and 0.75H each, C=CH), 6.93–7.28 (m, 5H, Ar-H and NH), 4.22 and 4.19 (s, 0.6H and 1.4H each, In-CH$_2$), 3.87 (s, 2H, NCH$_2$), 3.71 (s, 3H, OMe); $^{13}$C-NMR (CDCl$_3$) δ183.6 (C3), 172.0 (C5), 169.8 (C=O), 136.3, 127.3, 123.0, 121.9, 119.3, 119.2, 111.4, 111.3, 52.6 (OMe), 46.5 (NCH$_2$), 29.7 (InCH$_2$).

{3-[1-Phenyl-1-(tetrahydropyran-2-yloxy)-methyl]-[1,2,4]thiadiazol-5-ylamino}-acetic acid methyl ester or N-{3-[1-Phenyl-1-(tetrahydropyran-2-yloxy)-methyl][1,2,4]-thiadiazol-5-yl}glycine methyl ester; colorless oil, 89% yield. $^1$H-NMR (CDCl$_3$) δ (diastereoisomers) 7.45–7.55 (m, 2H, Ar-H), 7.23–7.40 (m, 3H, Ar-H), 7.00 and 6.65 (br. s, 0.5H and 0.5H each, NH), 5.91 and 5.87 (s, 0.5H and 0.5H each, αH), 4.85 and 4.66 (t, 0.5H and 0.5H each, OCHO), 4.06 (s, 2H, NCH$_2$), 3.78 (s, 3H, OMe), 3.52–4.05 (m, 2H, OCH$_2$), 1.56–1.92 (m, 6H, 3CH$_2$).

C. Proceeding in a similar manner as described in example 5A, the following compounds are prepared:

N-{3-methoxy-[1,2,4]-thiadiazol-5-yl}-leucine methyl ester

N-{3-methoxy-[1,2,4]-thiadiazol-5-yl}-isoleucine methyl ester

N-{3-methoxy-[1,2,4]-thiadiazol-5-yl}-alanine methyl ester

N-{3-methoxy-[1,2,4]-thiadiazol-5-yl}-proline methyl ester

N-{3-methoxy-[1,2,4]-thiadiazol-5-yl}-phenylalanine methyl ester

N-{3-methoxy-[1,2,4]-thiadiazol-5-yl}-tyrosine methyl ester

N-{3-methoxy-[1,2,4]-thiadiazol-5-yl}-serine methyl ester

N-{3-methoxy-[1,2,4]-thiadiazol-5-yl}-threonine methyl ester

D. Preparation of N-(3-methoxy-[1,2,4]thiadiazo-5-yl)-L-proline methyl ester.

To a suspension of L-proline methyl ester hydrochloride (331 mg, 2 mmol) in DMF (15 mL) was added triethylamine (0.56 mL, 4 mmol) and the resulting mixture was stirred for 10 min at room temperature. Then, a solution of 5-chloro-3-methoxy-[1,2,4]thiadiazole (151 mg, 1 mmol) in DMF (5 mL) was added dropwise The resulting reaction mixture was stirred at room temperature for 16 h. The mixture was diluted with water and ethyl acetate. The organic layer was collected, washed with brine, dried (sodium sulfate), filtered and concentrated in vacuo Purification by column chromatography on silica gel using a solvent mixture of hexane and ethyl acetate (1/1) afforded N-(3-methoxy-[1,2,4]thiadiazo-5-yl)-L-proline methyl ester (210 mg, 86.4%) as a light yellow oil. 1H-NMR (CDCl$_3$) δ4.50 (m, 1H, CHCO$_2$), 3.96 (s, 3H, OMe), 3.75 (s, 3H, OMe), 3.55 (m, 1H, NCHpro), 3.40 (m, 1H, NCHpro), 2.11–2.35 (m, 4H, 2CH$_2$pro).

EXAMPLE 6

A. Preparation of 2-(3-methoxy-[1,2,4]thiadiazol-5-ylamino)-acetamide or b-N-{3-methoxy-[1,2,4]-thiadiazol-5-yl}-glycinamide.

The ester (101 mg, 0.5 mmol) was stirred with aq. ammonia (0.5 mL of a 28–30% solution) for 30 min. Acetonitrile (15 mL) was added and volatile materials were removed in vacuo. The residue was purified by column chromatography on silica gel using a solvent mixture of dichloromethane and methanol (9/1) thereby affording 2-(3-methoxy-[1,2,4]thiadiazol-5-ylamino)-acetamide (92 mg, 98%) as a white solid.

B. In a similar manner as described in example 6A, the following compounds were prepared:

2-(3-n-Butoxy-[1,2,4]thiadiazol-5-ylamino)-acetamide or β-N-{3-n-butoxy-[1,2,4]-thiadiazol-5-yl)glycinamide; white solid, 95.7% yield. M.p. 148.5–149.5° C.; $^1$H-NMR (DMSO) δ8.51 (br. s,1H, NH), 7.51 (br. s,1H, NH), 7.14 (br. s,1H, NH), 4.18 (t, J=6.6 Hz, 2H, OCH$_2$), 3.88 (br. d, J=2.8 Hz, 2H, NCH$_2$), 1.63 (m, 2H, OCH$_2$CH$_2$), 1.38 (m, 2H, CH$_2$ CH$_3$), 0.90 (t, J=7.2 Hz, 3H, CH$_3$); $^{13}$C-NMR (DMSO) δ181.6 (C3), 169.9 (C=O), 167.1 (C5), 67.9 (OCH$_2$), 46.8 (NCH$_2$), 30.5, 18.6, 13.6; MS (m/z) 231 (M$^+$+1), 253, 231, 202, 175, 99, 83, 61.

2-[3-(3-Phenylallyl)-[1,2,4]thiadiazol-5-ylamino]-acetamide or β-N-{3-cinnamyl-[1,2,4]-thiadiazol-5-yl}-glycinamide; white solid, 85% yield. M.p. 150.0–152.5° C.; $^1$H-NMR (MeOD) δ7.37–7.39 (m, 2H, Ar-H), 7.27–7.31 (m, 2H, Ar-H), 7.18–7.22 (m, 1H, Ar-H), 6.42–6.55 (m, 2H, HC=CH), 4.09 (s, 2H, NCH$_2$), 3.59 (d, J=6.2 Hz, 2H, C=CCH$_2$); MS (m/z) 275 (M$^+$+1), 258, 230, 189, 152, 117, 91.

2-[3-(1H-Indol-3-ylmethyl)-[1,2,4]thiadiazol-5-ylamino]-acetamide or β-N-{3-3-(1H-Indol-3-ylmethyl)-[1,2,4]-thiadiazol-5-yl}-glycinamide; off-white solid, 94.0% yield. M.p. 200.0–200.5° C.; $^1$H-NMR (DMSO) δ8.46 (t, J=5.4 Hz, 1H, NH), 7.58 (d, J=7.9 Hz, 1H), 7.53 (br. s, 1H, NH), 7.35 (d, J=8.1 Hz, 1H), 7.20 (br. s, 1H), 7.07 (t, J=7.3

Hz, 1H), 6.97 (t, J=7.5 Hz, 1H), 4.04 (s, 2H, In-CH$_2$), 3.94 (d, J=5.4 Hz, 2H, NCH$_2$); $^{13}$C-NMR (DMSO) δ182.9 (C3), 171.7 (C5), 170.2 (C=O), 136.2, 127.2, 123.4, 120.9, 118.9, 118.3, 111.3, 110.5, 47.3 (NCH$_2$), 29.3 (InCH$_2$); MS (m/z) 288 (M$^+$+1), 271, 243, 184, 155, 130.

2-{3-[Phenyl-(tetrahydropyran-2-yloxy)-methyl]-[1,2,4]thiadiazol-5-ylamino}-acetamide or β-N-{3-[Phenyl-(tetrahydropyran-2-yloxy)-methyl])-[1,2,4]-thiadiazol-5-yl}-glycinamide; white solid, 80.2% yield. M.p. 147.5–148.5° C.; $^1$H-NMR (CDCl$_3$) δ (diastereoisomers) 7.50–7.52 (m, 3H, Ar-H), 7.28–7.38 (m, 2H, Ar-H), 6.82 and 6.68 (br. t, 0.5H and 0.5H each, NHCH$_2$), 6.08 and 5.98 (br. s, 0.5H and 0.5H each, NH), 5.92 and 5.87 (s, 0.5H and 0.5H each, αH), 5.68 (br. s, 1H, NH), 4.86 and 4.65 (t, J=3.7 Hz, 0.5H and 0.5H each, OCHO), 3.99 (t, J=6.5 Hz, 2H, NCH$_2$), 3.52–4.05 (m, 2H, OCH$_2$), 1.52–1.80 (m, 6H, 3CH$_2$).

C. In a similar manner as described in example 6A, the following compounds are prepared:

β-N-{3-n-butoxy-[1,2,4]-thiadiazol-5-yl}-alaninamide
β-N-{3-n-butoxy-[1,2,4]-thiadiazol-5-yl}phenylalaninamide
β-N-{3-n-butoxy-[1,2,4]-thiadiazol-5-yl}-leucinamide
β-N-{3-n-butoxy-[1,2,4]-thiadiazol-5-yl}-isoleucinamide
β-N-{3-n-butoxy-[1,2,4]-thiadiazol-5-yl}-tyrosinamide

EXAMPLE 7

A. Preparation of N-(3-methoxy-[1,2,4]thiadiazol-5-yl)-L-leucyl-L-proline methyl ester.

A solution of N-L-leucyl-L-proline methyl ester hydrochloride (5.6 g, 20 mmol, prepared according to the procedure by Jones, J. B. et al. in J. Med. Chem. 1995, 38, 3078) and triethylamine (5.6 mL, 40 mmol) in DMF (60 mL) was stirred at room temperature for 15 min. Then, a solution of 5-chloro-3-methoxy-[1,2,4]thiadiazole (1.51 g, 10 mmol) in DMF (10 mL) and tetrabutylammonium bromide (150 mg) were added and the resulting mixture was stirred at room temperature for 24 h. The reaction mixture was quenched with water and extracted into ethyl acetate. The organic layer was washed with a saturated solution of sodium bicarbonate, brine, dried (sodium sulfate), filtered and concentrated in vacuo. Purification by column chromatography on silica gel using a mixture of hexane and ethyl acetate (7/3 and 6/4) afforded N-(3-methoxy-[1,2,4]thiadiazol-5-yl)-L-leucyl-L-proline methyl ester (1.92 g, 53.9%) as as an off-white foam. $^1$H-NMR (CDCl$_3$) δ7.10 (d, J=8.5 Hz, 1H, NHCH), 4.74 (m, 1H, NHCH), 4.57 (dd, J=8.6, 4.6 Hz, 1H, CHCO$_2$), 3.92 (s, 3H, OMe), 3.85 (m, 1H), 3.69 (s, 3H, OMe), 3.62 (m, 1H), 2.17–2.23 (m, 1H), 1.95–2.07 (m, 4H), 1.77–1.82 (m, 1H), 1.59–1.66 (m,1H), 0.97 (d, J=6.5 Hz, 3H, Me), 0.94 (d, J=6.7 Hz, 3H, Me); MS (m/z) 357 (M$^+$+1), 228, 200, 130, 101, 70.

B. In a similar manner, the following compounds were prepared:

N-(3-Butoxy-[1,2,4]thiadiazol-5-yl)-L-leucyl-L-proline methyl ester, light yellow oil, 20.3% yield. 1H-NMR (CDCl$_3$) δ7.25 (d, J=8.8 Hz,1H, NHCH), 4.75 (m, 1H, NHCH, 4.58 (dd, J=8.6, 4.6 Hz, 1H, CHCO$_2$), 4.23 (t, J=6.8 Hz, 2H, OCH$_2$), 3.92 (m, 1H), 3.61–3.72 (m, 1H), 3.69 (s, 3H, OMe), 2.20–2.25 (m, 1H), 1.98–2.06 (m, 3H), 1.63–1.82 (m, 5H), 1.39–1.45 (m, 2H), 0.90–0.97 (m, 9H, 3Me).

N-(3-Phenyl-[1,2,4]thiadiazol-5-yl)-L-leucyl-L-proline methyl ester, white solid, 85% yield. M.p. 154.0–154.5° C.; $^1$H-NMR (CDCl$_3$) d 8.14–8.16 (m, 2H, Ar-H), 7.83 (d, J=8.7 Hz, 1H, NHCH), 7.40–7.42 (m, 3H, Ar-H), 5.02 (m, 1H, NHCH), 4.68 (dd, J=8.6, 4.6 Hz, 1H, CHCO$_2$), 4.09–4.14 (m, 1H), 3.77–3.82 (m, 1H), 3.76 (s, 3H, OMe), 1.72–2.29 (m, 7H), 1.09 (d, J=6.5 Hz, 3H, Me), 0.98 (d, J=6.6 Hz, 3H, Me).

N-(3-Methyl-[1,2,4]thiadiazol-5-yl)-L-leucyl-L-proline methyl ester, white solid, 30% yield. M.p. 88–89° C.; $^1$H-NMR (CDCl$_3$) δ7.80 (d, J=8.6 Hz, 1H, NHCH), 4.68 (m, 1H, NHCH), 4.58 (dd, J=8.6, 4.6 Hz, 1H, CHCO$_2$), 3.94–3.98 (m, 1H), 3.62–3.68 (m, 1H), 3.68 (s, 3H, OMe), 2.31 (s, 3H, Me), 2.07–2.22 (m, 1H), 1.96–2.07 (m, 3H), 1.69–1.79 (m, 4H), 0.96 (d, J=6.6 Hz, 3H, Me), 0.94 (d, J=6.7 Hz, 3H, Me).

C. Proceeding in a similar manner as described in example 7A, the following compounds are prepared:

N-(3-Methoxy-[1,2,4]thiadiazol-5-yl)-L-leucyl-L-octahydro-(3aS, 6aS)-cyclopentan[b]pyrrole-2(S)-carboxylic acid methyl ester N-(3-Methoxy-[1,2,4]thiadiazol-5-yl)-L-leucyl-{4-tert-butoxycarbonyl}piperazine-2(R or S)-carboxylic acid methyl ester N-(3-Methoxy-[1,2,4]thiadiazol-5-yl)-L-leucyl-decahydro-(4aR,8aS)-isoquinoline-3(S)-carboxic acid methyl ester N-(3-Methoxy-[1,2,4]thiadiazol-5-yl)-L-leucyl-L-octahydroindole-2-carboxylic acid methyl ester N-(3-Methoxy-[1,2,4]thiadiazol-5-yl)-L-leucyl-L-indoline-2-carboxylic acid methyl ester N-(3-Methoxy-[1,2,4]thiadiazol-5-yl)-L-isoleucyl-L-octahydroindole-2-carboxylic acid methyl ester N-(3-Methoxy-[1,2,4]thiadiazol-5-yl)-L-isoleucyl-L-L-octahydro-(3aS, 6aS)-cyclopentan[b]pyrrole-2(S)-carboxylic acid methyl ester.

EXAMPLE 8

Preparation of N-(3-chloromethyl-[1,2,4]thiadiazol-5-yl)-L-leucyl-L-proline methyl ester.

A solution of N-L-leucyl-L-proline methyl ester hydrochloride (2.22 g, 8 mmol) and triethylamine (2.8 mL, 20 mmol) in DMF (50 mL) was stirred at room temperature for 15 min. Then, a solution of 3-chloromethyl-5-chloro-[1,2,4]thiadiazole (0.34 g, 2 mmol) in DMF (10 mL) and tetra-butylammonium bromide (100 mg) were added and the resulting mixture was stirred at room temperature for 24 h. The reaction mixture was quenched with water and extracted into ethyl acetate. The organic layer was washed with a saturated ammonium chloride solution, brine, dried (sodium sulfate), filtered and concentrated in vacuo. Purification by column chromatography on silica gel using a mixture of hexane and ethyl acetate (7/3, 6/4 and 1/1) afforded N-(3-chloromethyl-[1,2,4]thiadiazol-5-yl)-L-leucyl-L-proline methyl ester as a white foam, 0.49 g, 65.3% yield. $^1$H-NMR (CDCl$_3$) δ7.56 (d, J=8.2 Hz, 1H, NHCH), 4.78 (m, 1H, NHCH), 4.60 (dd, J=8.5, 4.6 Hz, 1H, CHCO$_2$), 4.46 (s, 2H, CH$_2$Cl), 4.09 (m, 1H), 3.69–3.73 (m, 1H), 3.74 (s, 3H, OMe), 2.25–2.30 (m, 1H), 1.68–2.11 (m, 6H), 0.99–1.03 (2d, 6H, 2Me); MS (m/z) 375 (M$^+$+1), 357, 305, 246, 218, 162, 150, 130.

EXAMPLE 9

Preparation of N-{3-[1-[4-(2-pyridyl)piperazinyl]-methyl]-[1,2,4]thiadiazol-5-yl}-L-leucyl-L-proline methyl ester.

A mixture of N-(3-chloromethyl-[1,2,4]thiadiazol-5-yl)-L-leucyl-L-proline methyl ester (0.45 g, 1.2 mmol), 1-(2-pyridyl)piperazine (0.62 mL, 4 mmol), triethylamine (1.2 mL, 8 mmol) and tetra-butylammonium bromide (100 mg) in DMF (20 mL) was stirred at room temperature for 24 h. The reaction mixture was diluted with water and ethyl acetate. The organic layer was collected, washed with water, dried (sodium sulfate), filtered and concentrated in vacuo to give a light yellow oil. Purification by column chromatography on silica gel using a solvent mixture of 5% methanol in dichloromethane afforded N-{3-[1-[4-(2-pyridyl)piperazinyl]-methyl]-[1,2,4]thiadiazol-5-yl}-L-leucyl-L-proline methyl ester as a white foam (0.55 g, 91.7 %). $^1$H-NMR (CDCl$_3$) δ8.19 (m, 1H), 7.48–7.52 (m, 1H), 7.14 (br. m, 1H, NH), 6.64–6.67 (m, 2H), 4.67 (m, 1H, CHCO), 4.57 (dd, J=8.4 and 4.6 Hz, 1H, CHCO$_2$), 3.92 (m, 1H, NCHpro), 3.62–3.78 (m, 1OH, OMe, NCHpro, N=CCH$_2$, 2NCH$_2$), 2.83 (m, 4H, 2NCH$_2$), 1.62–2.30 (m, 6H, 2CH$_2$pro and CH$_2$), 0.90–1.03 (2d, J=6.5 and 6.6 Hz, 7H, 2Me and 1CH); MS (m/z) 502 (M$^+$+1), 459, 408, 382, 300, 253, 225, 176, 147, 121, 95.

EXAMPLE 10
Preparation of N,N'-{3-methylene-[1,2,4]thiadiazol-5-yl}-di-{L-leucyl-L-proline methyl ester}.

A solution of N-L-leucyl-L-proline methyl ester hydrochloride (2.22 g, 8 mmol) and triethylamine (2.8 mL, 20 mmol) in DMF (50 mL) was stirred at room temperature for 15 min. Then, a solution of 3-chloromethyl-5-chloro-[1,2,4]thiadiazole (0.34 g, 2 mmol) in DMF (10 mL) and tetra-butylammonium bromide (100 mg) were added and the resulting mixture was heated at 75–78° C. for 19 h. The reaction mixture was quenched with water and extracted into ethyl acetate. The organic layer was washed with water, dried (sodium sulfate), filtered and concentrated in vacuo to a brown solid. Purification by column chromatography on silica gel using a mixture of dichloromethane and ethyl acetate (1/1) followed by a mixture of dichloromethane and methanol (95/5) afforded N,N'-{3-methylene-[1,2,4]thiadiazol-5-yl}-di-{L-leucyl-L-proline methyl ester}as a light yellow semi-solid (0.43 g, 37.1%). $^1$H-NMR (CDCl$_3$) δ6.83 (d, J=6.8 Hz, 1H, SCNH), 4.78 (m, 1H, CHCO), 4.61 (dd, J=8.7 and 4.8 Hz, 1H, CHCO$_2$), 4.59 (m, 1H, CHCO), 4.42 (dd, J=8.3 and 4.1 Hz, 1H, CHCO$_2$), 3.73 (s, 3H, OMe), 3.71 (s, 3H, OMe), 3.68 (m, 2H, N=CCH$_2$), 3.38– 3.70 (m, 5H, 2NCH$_2$pro and NH), 1.38–2.40 (m, 12H, 4CH$_2$pro and 2CH$_2$), 0.85–1.05 (4d, J=6.5, 6.7, 6.7 and 6.4 Hz, 14H, 4Me and 2CH); MS (m/z) 581 (M$^+$+1), 549, 452, 424, 392, 295, 267, 211, 130.

EXAMPLE 11
A. Preparation of N-(3-methoxy-[1,2,4]thiadiazol-5-yl)-L-leucyl-L-proline.

To an ice-cooled solution of N-(3-methoxy-[1,2,4]thiadiazol-5-yl)-L-leucyl-L-proline methyl ester (0.68 g, 1.91 mmol) in methanol (10 mL) was added a solution of 1N sodium hydroxide (2.4 mL, 2.4 mmol). The resulting mixture was stirred in ice for 3 h, then at room temperature for 16 h. Volatile materials were removed in vacuo and the residue was dissolved in water (10 mL) and washed with ethyl acetate. The aqueous layer was collected and acidified with 1N HCl solution (pH ca. 5.6) as a voluminous white precipitate separated. The mixture was extracted into ethyl acetate (6×25 mL), and the combined organic layers was dried (sodium sulfate), filtered and concentrated to a light yellow foam. Trituration with diethyl ether gave N-(3-methoxy-[1,2,4]thiadiazol-5-yl)-L-leucyl-L-proline as a white solid (0.58 g, 89%). M.p. foamed at 78° C. and melted at 89.0–92.0C.; $^1$H-NMR (CDCl$_3$) δ7.65 (br. s, 1H, NHCH), 4.70 (br. t, 1H, NHCH), 4.49 (t, J=5.3 Hz, 1H, CHCO$_2$), 3.97 (s, 3H, OMe), 3.56–3.58 (m, 2H), 2.03–2.21 (m, 3H), 1.60–1.76 (m, 3H), 0.76–0.99 (m, 1H), 0.99 (d, J=6.5 Hz, 3H, Me), 0.96 (d, J=6.2 Hz, 3H, Me); MS (m/z) 343 (M$^+$+1), 228, 200, 102, 83.

B. In a similar manner, the following compounds were prepared:

N-(3-Butoxy-[1,2,4]thiadiazol-5-yl)-L-leucyl-L-proline, white solid, 95.8% yield. M.p. foamed at 78° C. and melted at 110.0–113.0° C.; $^1$H-NMR (CDCl$_3$) δ7.90 (br. s, 1H, NHCH), 4.50–4.70 (m, 1H, NHCH), 4.45 (dd, J=7.1, 3.4 Hz, 1H; CHCO$_2$), 4.26 (t, J=6.7 Hz, 2H, OCH), 3.92 (m, 1H), 3.53–3.61 (m, 1H), 1.85–2.35 (m, 5H), 1.67–1.76 (m, 3H), 1.55–1.62 (m, 1H), 1.39–1.48 (m, 2H), 0.85–0.97 (m,1 OH, 3Me and 1CH); MS (m/z) 385 (M$^+$+1), 329, 270, 242, 214, 116, 70.

N-(3-Phenyl-[1,2,4]thiadiazol-5-yl)-L-leucyl-L-proline, white solid, 91.8% yield. M.p. foamed at 112° C. and melted at 136.0–138.0° C.;$^1$H-NMR (CDCl$_3$) δ8.08–8.12 (m, 2H, Ar-H), 7.58 (br. s, 1H, NHCH), 7.38–7.42 (m, 3H, Ar-H), 4.90 (m, 1H, NHCH), 4.53 (m, 1H, CHCO$_2$), 4.09–4.14 (m, 1H), 3.52–3.62 (m, 1H), 2.00–2.32 (m, 4H), 1.75–1.95 (m, 2H), 1.55–1.64 (m, 1H), 1.04 (d, J=5.9 Hz, 3H, Me), 0.99 (d, J=6.0 Hz, 3H, Me), 0.85–0.92 (m, 1H); MS (m/z) 389 (M$^+$+1), 333, 274, 246, 190, 116, 70.

N-(3-Methyl-[1,2,4]thiadiazol-5-yl)-L-leucyl-L-proline, white solid, 80% yield. M.p. foamed at 81° C. and melted at 112–115° C.; $^1$H-NMR (CDCl$_3$) d 7.30 (br. s, NHCH), 4.42–460 (m,1H, NHCH), 3.80–4.00 (m,1H, CHCO$_2$), 3.54–3.65 (m,1H), 2.37 (s, 3H, Me), 2.07–2.42 (m, 5H), 1.50–1.90 (m, 4H), 0.96–1.10 (m, 6H, 2Me), 0.80–0.95 (m, 1H); MS (m/z) 327 (M$^+$+1), 271, 212, 184, 116, 70.

N-{3-[1-(4-(2-Pyridyl)piperazin-1-yl)-methyl]-[1,2,4]thiadiazol-5-yl}-L-leucyl-L-proline, light yellow solid, 70.7% yield. M.p. 163.5–166.0° C.; $^1$H-NMR (CDCl$_3$) δ8.21 (m,1H), 7.46–7.49 (m,1H), 6.60–6.65 (m, 2H), 4.20–4.70 (m, 2H, CHCO and CHCO$_2$), 3.80 (m, 1H, NCHpro), 3.40–3.75 (m, 7H, NCHpro, N=CCH$_2$, 2NCH$_2$), 2.72 (m, 4H, 2NCH), 1.60–2.05 (m, 6H, 2CH$_2$pro and CH$_2$), 0.90–1.03 (2d, J=5.5 and 5.7 Hz, 7H, 2Me and 1CH); MS (m/z) 488 (M$^+$+1), 442, 368, 345, 297, 253, 225, 176, 147, 121.

N,N'{3-methylene-[1,2,4]thiadiazol-5-yl}-di-L-leucyl-L-proline}, light yellow solid (84.2%). M.p.; $^1$H-NMR (CDCl$_3$) δ6.83 (d, J=6.8 Hz, 1H, SCNH), 4.78 (m, 1H, CHCO), 4.61 (dd, J=8.7 and 4.8 Hz, 1H, CHCO$_2$), 4.59 (m, 1H, CHCO), 4.42 (dd, J=8.3 and 4.1 Hz, 1H, CHCO$_2$), 3.68 (m, 2H, N=CCH$_2$), 3.38–3.70 (m, 5H, 2NCH$_2$pro and NH), 1.38–2.40 (m, 12H, 4C$_2$H pro and 2C$_2$H ), 0.85–1.05 (4d, J=6.5, 6.7, 6.7 and 6.4 Hz, 14H, 4Me and 2CH); MS (m/z) 553 (M$^+$+1).

C. Proceeding in a similar manner, the following compounds are made:

N-(3-Methoxy-[1,2,4]thiadiazol-5-yl)-L-leucyl-L-octahydro-(3aS, 6aS)-cyclopentan[b]pyrrole-2(S)-carboxylic acid N-(3-Methoxy-[1,2,4]thiadiazol-5-yl)-L-leucyl-{4-tert-butoxycarbonyl}piperazine-2(R or S)-carboxylic acid N-(3-Methoxy-[1,2,4]thiadiazol-5-yl)-L-leucyl-decahydro-(4aR,8aS)-isoquinoline-3(S)-carboxic acid N-(3-Methoxy-[1,2,4]thiadiazol-5-yl)-L-leucyl-L-octahydroindole-2-carboxylic acid N-(3-Methoxy-[1,2,4]thiadiazol-5-yl)-L-leucyl-L-indoline-2-carboxylic acid N-(3-Methoxy-[1,2,4]thiadiazol-5-yl)-L-isoleucyl-L-octahydroindole-2-carboxylic acid N-(3-Methoxy-[1,2,4]thiadiazol-5-yl)-L-isoleucyl-L-L-octahydro-(3aS, 6aS)-cyclopentan[b]pyrrole-2(S)-carboxylic acid.

EXAMPLE 12
A. Preparation of N-(3-methoxy-[1,2,4]thiadiazol-5-yl)-L-iso-leucyl-L-proline methyl ester.

To a solution of N-L-iso-leucyl-L-proline methyl ester hydrochloride (5.58 g, 20 mmol, prepared according to a procedure reported by Jones, J. B. et al. in J. Med. Chem. 1995, 38, 3078) in DMF (50 mL) was added triethylamine (5.6 mL, 40 mmol), tetra-butylammonium bromide (0.4 g) and 5-chloro-3-methoxy-1,2,4-thiadiazole (1.51 g, 10 mmol). The resulting mixture was stirred at room tempearture for 16 h. The reaction mixture was diluted with water and ethyl acetate. The organic layer was collected, dried (sodium sulfate), filtered and concentrated in vacuo. The residue was purified by column chromatography on silica gel using a solvent mixture of hexane and ethyl acetate (7/3 and 6/4) thereby affording the title compound as a light yellow oil. Trituration with hexane and filtration gave N-(3-methoxy-[1,2,4]thiadiazol-5-yl)-L-iso-leucyl-L-proline methyl ester as a white solid (3.1 g, 87.1%). M.p. 129–130° C.; $^1$H-NMR (CDCl$_3$) δ7.90 (d, J=9.2 Hz, 1H, NHCH), 4.61–4.65 (m, 2H, NHCH and CHCO$_2$), 3.96–4.00 (m, 1H), 3.92 (s, 3H, OMe), 3.69–3.72 (m, 1H), 3.72 (s, 3H, OMe), 2.21–2.24 (m, 1H), 1.82–2.05 (m, 4H), 1.62–1.66 (m, 1H), 1.18–1.24 (m, 1H), 1.03 (d, J=6.8 Hz, 3H, Me), 0.88 (t, J=7.2 Hz, 3H, Me).

B. In a similar fashion, N-[3-(1-phenyl-1-tetrahydropyran-2-yloxy)methyl-[1,2,4]thiadiazol-5-yl]-L-iso-leucyl-L-proline methyl ester was prepared as a white foam in 54.7% yield. $^1$H-NMR (CDCl$_3$) δ7.46–7.50 (m, 2H), 7.26–7.36 (m, 4H, Ar-H and NH), 5.79–5.85 (m, 1H, αH), 4.58–4.95 (m, 1H,OCHO), 4.38–4.51 (m, 2H), 3.81–4.02 (m, 2H), 3.74 (s, 3H, OMe), 3.60–3.70 (m, 1H), 3.45–3.55 (m, 1H), 1.45–2.10 (m, 12H), 1.04 (d, J=6.6 Hz, 3H, Me), 0.90 (t, J=7.3 Hz, 3H, Me).

EXAMPLE 13
Preparation of N-(3-methoxy-[1,2,4]thiadiazol-5-yl)-L-iso-leucyl-L-proline In a similar manner as described in example 18A, base saponification of N-(3-methoxy-[1,2,4]thiadiazol-5-yl)-L-iso-leucyl-L-proline methyl ester followed by acidification, afforded N-(3-methoxy-[1,2,4]thiadiazol-5-yl)-L-iso-leucyl-L-proline (93.3% yield) as a white solid. M.p. foamed at 85° C. and melted at 112–114° C.; $^1$H-NMR (CDCl$_3$) δ7.40–7.90 (br, 1H, NHCH), 4.50–4.60 (m, 2H, NHCH and CHCO$_2$), 3.90–4.10 (m, 1H), 3.96 (s, 3H, OMe), 3.69–3.72 (m, 1H), 1.82–2.25 (m, 4H), 1.62–1.75 (m, 1H), 1.15–1.32 (m, 1H), 1.02 (d, J=6.7 Hz, 3H, Me), 0.88 (t, J=6.6 Hz, 3H, Me); MS (m/z) 343 (M$^+$+1), 287, 228, 200, 116, 70.

EXAMPLE 14
A. Preparation of N-[3-(1-Phenyl-1-hydroxy)methyl-[1,2,4]thiadiazol-5-yl]-L-iso-leucyl-L-proline methyl ester.

A solution of N-[3-(1-Phenyl-1-(tetrahydropyran-2-yloxy))methyl-[1,2,4]thiadiazol-5-yl]-L-iso-leucyl-L-proline methyl ester (0.9 g, 1.74 mmol ) in methanol (5 m) and 3N HCl (10 mL) was stirred at room temperature for 5 min. Methanol was reduced under reduced pressure. The reaction mixture was diluted with ethyl acetate and basified with 3N sodium hydroxide solution (pH ca. 10). The organic layer was collected, washed with water, dried (sodium sulfate), filtered and concentrated in vacuo. The material was purified by column chromatography (60% EtOAc: heaxane) to give the titled compound (0.72 g, 95.6% yield) as a white foam, 95.6% yield. $^1$H-NMR (CDCl$_3$) δ7.28–7.46 (m, 6H, 5Ar-H and NH), 5.75–5.85 (m, 1H, αH), 4.40–4.60 (m, 2H), 3.58–3.95 (m, 3H), 3.72 (s, 3H, OMe), 1.85–2.20 (m, 4H), 1.62–1.82 (m, 2H), 1.14–1.32 (m, 1H), 1.04 (d, J=6.3 Hz, 3H, Me), 0.91 (t, J=7.0 Hz, 3H, Me).

B. In a similar manner, the following compounds was prepared:

N-[3-(1-phenyl-1-hydroxy)methyl-[1,2,4]thiadiazol-5-yl]-L-iso-leucyl-L-proline as a white solid in 76% yield. M.p. foamed at 100° C. and melted at 163–166° C.; $^1$H-NMR (CDCl$_3$) δ7.79 (br, 1H, NH), 7.38–7.48 (m, 2H), 7.26–7.36 (m, 3H, Ar-H), 5.69–5.74 (m, 1H, αH), 3.50–4.50 (m, 3H),1.80–2.20 (m, 6H), 1.60–1.780 (m, 1H), 1.10–1.30 (m, 1H), 0.91 (d, J=5.7 Hz, 3H, Me), 0.87 (t, J=7.5 Hz, 3H, Me); MS (m/z)419 (M$^+$+1), 401, 349, 304, 242, 218, 163, 107, 83.

EXAMPLE 15
A. Preparation of N-[3-Benzoyl-[1,2,4]thiadiazol-5-yl]-L-iso-leucyl-L-proline methyl ester.

To an ice-cooled suspension the compound from example 14A (0.65 g, 1.25 mmol) in acetone (10 ml) was added dropwise over a period of ca. 10 min a solution of chromium trioxide (0.15 g, 1.5 mmol) dissolved in water (10 mL) and conc. sulfuric acid (0.13 mL). The resulting mixture was allowed to warm to room temperature and stirred for 16 h. The reaction mixture was diluted with ethyl acetate (100 mL), then made basic (pH ca. 10) by the addition of 3N sodium hydroxide solution. The organic layer was collected, washed with water, dried (sodium sulfate), filtered and concentrated in vacuo. Purification by column chromatography on silica gel using a solvent gradient of a mixture of hexane and ethyl acetate (6/4 and 4/6) afforded the title compound (0.63 g mg, 92.3%) as a colorless oil. $^1$H-NMR (CDCl$_3$) δ8.16 (d, J=7.5 Hz, 2H), 8.08 (d, J=8.4 Hz,1H, NH), 7.59 (t, J=7.2 Hz,1H), 7.44 (t, J=7.6 Hz, 2H), 4.62–4.66 (m, 2H), 4.30–4.32 (m, 1H), 3.76 (s, 3H, OMe), 3.75–3.80 (m, 1H), 2.24–2.30 (m, 1H), 1.95–2.10 (m, 5H), 1.76–1.78 (m, 1H), 1.28–1.34 (m, 1H), 1.13 (d, J=6.6 Hz, 3H, Me), 0.96 (t, J=7.4 Hz, 3H, Me).

B. In a similar fashion, the following compounds were prepared:

2-(3-Benzoyl-[1,2,4]thiadiazol-5-ylamino)-acetamide or β-N-{3-benzoyl-1,2,4-thiadiazol-5-yl}-glycinamide, white solid, 46.2% yield. M.p. 227–228° C.; $^1$H-NMR (DMSO) δ8.84 (br. s, 1H, NH), 8.03–8.05 (m, 2H), 7.69 (t, J=6.8 Hz,1H, NHCH$_2$), 7.54–7.57 (m, 3H), 7.19 (br. s, 1H, NH), 4.02 (d, J=5.3 Hz, 2H, NCH$_3$); MS m/z263 (M$^+$+1), 246, 218, 185, 158, 140, 105.

EXAMPLE 16
Preparation of N-[3-benzoyl-[1,2,4]thiadiazol-5-yl]-L-iso-leucyl-L-proline.

Proceeding in a similar manner as described in example 11, saponification of the ester from example 15A followed by acidification afforded N-[3-benzoyl-[1,2,4]thiadiazol-5-yl]-L-iso7leucyl-L-proline as a white solid in 93.8% yield. M.p. foamed at 103° C. and melted at 132–134° C.; $^1$H-NMR (CDCl$_3$) δ8.15 (br. s, 1H, NH), 8.13 (d, J=7.6 Hz, 2H), 7.55 (t, J=7.0 Hz, 1H), 7.42 (t, J=7.8 Hz, 2H), 4.58–4.62 (m, 1H), 4.55 (dd, J=7.6, 4.0 Hz, 1H), 4.18–4.22 (m, 1H), 3.58–3.63 (m, 1H), 1.92–2.2 (m, 6H), 1.65–1.75 (m, 1H), 1.21–1.30 (m, 1H), 0.98 (d, J=6.8 Hz, 3H, Me), 0.90 (t, J=7.4 Hz, 3H, Me); MS m/z 417 (M$^+$+1), 371, 302, 274, 206, 116, 70.

EXAMPLE 17
Preparation of {3-methoxy-[1,2,4]-thiadiazol-5-yl}carbamoyl-L-leucine-L-proline methyl ester.

To 5-amino-3-methoxy-[1,2,4]thiadiazole (1.31 g, 10 mmol) in dichloromethane (15 mL) at room temperature was added 1,1'-carbonyldiimidazole, CDI, (1.78 g,11 mmol) followed by triethylamine (2.1 mL, 15 mmol). The resulting suspension was stirred under nitrogen for 2.5 h. Volatile materials were removed in vacuo and the residue was dissolved in DMF (20 mL). The latter was then added to a solution of L-leucine-L-proline methyl ester hydrochloride (4.18 g, 15 mmol) and triethyl amine (2.1 mL, 15.1 mmol) in DMF (25 mL). The resulting mixture was heated at 120° C. for 2 h and then allowed to cool to room temperature. Volatile materials were removed in vacuo and the residue was diluted with ethyl acetate (250 mL) and water (100 mL). The aqueous layer was extracted with ethyl acetate (2×100 mL). The combined organic layers was dried (sodium sulfate), filtered and concentrated in vacuo. Purification by column chromatography on silica gel using a solvent mixture of hexane and ethyl acetate (1/1 and 2/3) afforded {3-methoxy-[1,2,4]-thiadiazol-5-yl}carbamoyl-L-leucine-L-proline methyl ester as a light yellow foam (3.2 g, 76.6%). M.p. 88–90° C.; $^1$H-NMR (CDCl$_3$) δ12.75 (s, 1H, NH), 6.70 (d, J=12.0 Hz, 1H, NH), 4.79–4.87 (m, 1H, NCHpro), 4.54–4.59 (dd, J=11.8, 6.0 Hz, 1H, NCH), 4.12 (s, 3H, OMe), 3.64–3.90 (m, 2H, NCH$_2$pro), 1.56–2.26 (m, 6H, 3CH$_2$), 0.94–1.12 (two d, J=9.7 Hz, 7H, 2CH$_3$+CH); $^{13}$C-NMR (CDCl$_3$) δ178.3 (C3), 172.3, 171.1 (CO$_2$), 165.9 (C5), 153.7 (NHC=ONH), 58.8, 56.6, 52.2, 49.8, 47.0 (CH$_2$), 42.0 (CH$_2$), 29.0 (CH$_2$), 24.8 (CH$_2$), 24.5, 23.2, 22.0; MS (m/z) 400 (M$^+$+1), 326, 271, 243, 209, 158, 130, 87.

EXAMPLE 18
Preparation of {3-methoxy-[1,2,4]-thiadiazol-5-yl}carbamoyl-L-leucine-L-proline.

In a similar manner as shown in example 18, base saponification of 3-methoxy-5-(N-L-leucine-L-proline)carbamoyl-[1,2,4]-thiadiazole methyl ester using a solution of 1N sodium hydroxide followed by acidification using a solution of 1N HCl {3-methoxy-[1,2,4]-thiadiazol-5-yl}carbamoyl-L-leucine-L-proline as a white solid (55%). M.p. 209–21 1° C.; $^1$H-NMR (MeOD) δ4.64–4.67 (dd, J=8.1, 2.3 Hz, 1H, NCH), 4.44–4.45 (m, 1H, NCHpro), 3.94 (s, 3H, OMe), 3.60–3.86 (m, 2H, NCH$_2$pro), 1.54–2.27 (m, 6H, 3CH$_2$), 0.94–1.01 (two d, J=6.4 Hz, 7H, 2CH$_3$+CH); MS (m/z) 386 (M$^+$+1), 271, 229, 158, 116, 86.

EXAMPLE 19
Preparation of 3-methoxy-5-(N-carbobenzyloxy-L-phenylalanyl-L-alaninamido)-[1,2,4]thiadiazole To a solution of 5-amino-3-methoxy-[1,2,4]thiadiazole (0.37 g, 2.8 mmol) and N-carbobenzyloxy-L-phenylalanyl-L-alanine, N-Cbz-Phe-Ala-OH, (1.0 g, 2.7 mmol) in DMF (25 mL) was added 1,3-dicyclohexylcarbodiimide, DCC, (0.56 g, 2.7 mmol). After stirring for 30 min, 1-hydroxybenzotriazole hydrate, HOBT, (0.36 g, 2.7 mmol) was added and the resulting mixture was stirred at room temperature for 20 h. Volatile materials were removed in vacuo and the residue was purified by column chromatography on silica gel using a solvent mixture of dichloromethane and methanol (96/4) thereby affording the title compound as a white solid (1.2 g). Further purification by cristallization and chromatography on silica gel gave 3-methoxy-5-(N-carbobenzyloxy-L-phenylalanyl-L-alaninamido]-[1,2,4]thiadiazole (0.87 g, 67% yield). M.p. 161–162° C.; $^1$H-NMR (CDCl$_3$) δ7.14–7.38 (m, 12H, 10Ar-H and 2 NH), 5.92 (br. s, 1H, NH), 5.06 (s, 2H, OCH), 4.38 (m, 1H, CHCH$_2$Ar), 4.00 (m, 1H, CHCH$_3$), 3.97 (s, 3H, OMe), 3.00–3.08 (m, 2H, CHCH$_2$Ar), 1.34 (d, J=8.9 Hz, 3H, Me); MS (m/z) 484 (M$^+$+1), 416, 361, 316, 285, 185, 132, 75. The latter compound was also prepared by using diphenylphosphoryl azide and triethylamine instead of DCC/HOBT in 27.7% yield.

EXAMPLE 20
Preparation of 3-methoxy-5-(N-carbobenzyloxy-L-phenylalaninamido)-[1,2,4]thiadiazole.

To an ice-cooled solution of 5-amino-3-methoxy-[1,2,4] thiadiazole (1.31 g, 10 mmol) and N-carbobenzyloxy-L-phenylalanine, (Cbz-L-phe-OH 2.99 g, 10 mmol) in DMF (100 mL) was added 1,3-dicyclohexylcarbodiimide (2.06 g, 10 mmol) followed by 1-hydroxybenzotriazole hydrate (1.35 g, 10 mmol). The resulting mixture was stirred at room temperature for 16 h. The mixture was diluted with ethyl acetate (250 mL) and water (200 mL). The organic layer was collected and successively washed with a solution of 1N HCl (15 mL), water, a saturated solution of sodium bicarbonate, and water. The organic layer was dried (sodium sulfate), filtered and concentrated in vacuo. Purification by column chromatography using a solvent mixture of hexane and ethyl acetate (3/1) afforded 3-methoxy-5-(N-carbobenzyloxy-L-phenylalaninamido)-[1,2,4]thiadiazole as a colorless oil. Crystallization from ether and hexane gave the product as a white solid (1.1 g, 26.7%). $^1$H-NMR (CDCl$_3$) δ12.50 (s, 1H, NH), 7.06–7.35 (m, 10H, Ar-H), 6.02 (br. d, J=7.6 Hz, 1H, NH), 5.19–5.22 (m, 1H, CH), 5.11 (s, 2H, OCH$_2$), 4.05 (s, 3H, OMe), 3.11–3.20 (m, 2H, CHCH$_2$Ar); MS (m/z) 413 (M$^+$+1), 369, 222, 210, 132, 91.

EXAMPLE 21
Preparation of 3,5-di-(N-carbobenzyloxy-L-phenylalaninamido)-[1,2,4]thiadiazole.

To an ice-cooled solution of 3,5-diamino-[1,2,4]thiadiazole (1.16 g, 10 mmol, prepared according to the procedure reported by Kurzer, F. In J. Chem. Soc. 1955, 1) and N-carbobenzyloxy-L-phenylalanine, (Cbz-L-phe-OH, 4.98 g, 20 mmol) in DMF (100 mL) was added 1,3-dicyclohexylcarbodiimide (4.12 g, 20 mmol) followed by 1-hydroxybenzotriazole hydrate (2.70 g, 20 mmol). The resulting mixture was stirred at room temperature for 16 h. The mixture was diluted with ethyl acetate and water. The organic layer was collected and successively washed with a solution of 1N HCl, brine, a saturated solution of sodium bicarbonate and brine. The organic layer was dried (sodium sulfate), filtered and concentrated in vacuo to give a light yellow solid. Purification by column chromatography using a solvent mixture of hexane and ethyl acetate (7/3 and 6/4) afforded 3,5-di-(N-carbobenzyloxy-L-phenylalanylamido)-[1,2,4]thiadiazole as a white solid. Recrystallization from ethyl acetate and hexane gave the product as a white solid (3.5 g, 51.5%). M.p. 192–194° C.; $^1$H-NMR (CDCl$_3$) δ13.3 (s, 1H, NH), 11.1 (s, 1H, NH), 7.95 (d, J=7.5 Hz, 1H, NHCH), 7.68 (d, J=8.4 Hz, 1H, NHCH), 7.19–7.39 (m, 20H, Ar-H), 4.98 (s, 4H, 2OCH$_2$), 4.58–4.64 (m, 2H, 2CHCH$_2$), 3.03–3.12 (m, 2H, PhCH$_2$CH), 2.77–2.92 (m, 2H, PhCH$_2$CH); MS (m/z) 679.5 (M$^+$+1), 635, 591, 488, 445, 398, 354, 297, 210, 117.

EXAMPLE 22
Preparation of 5-bromoacetamido-3-methoxy-[1,2,4]thiadiazole.

To an ice-cooled solution of 5-amino-3-methoxy-[1,2,4]thiadiazole (1.31 g, 10 mmol) in THF (25 mL) was added triethylamine (2.22 g, 11 mmol) followed by dropwise addition of bromoacetyl bromide (1.52 g, 15 mmol). The resulting mixture was stirred at room temperature for 16 h. The mixture was diluted with water (25 mL) and ethyl acetate (50 mL). The aqueous layer was extracted with ethyl acetate (3×50 mL). The combined organic layers was dried (sodium sulfate), filtered and concentrated in vacuo. Purification by column chromatography on silica gel using a solvent gradient of a mixture of dichloromethane and methanol (98/2, 97/3 and 96/4) afforded 3-methoxy-5-bromoacetamido-[1,2,4]thiadiazole as a white solid (1.26 g, 50%). M.p. 198–199° C.; $^1$H-NMR (CDCl$_3$) δ13.10 (br. s, 1H, NH), 4.28 (s, 2H, CH$_2$), 4.11 (s, H, OMe); $^{13}$C-NMR (CDCl$_3$) δ176.8 (C3), 166.9 (C5), 166.6 (C=O), 56.9 (OMe), 25.9 (CH$_2$).

B. Similarly, when chloroacetyl chloride was used, 5-chloroacetamido-3-methoxy-[1,2,4]thiadiazole was obtained as a white solid (52%). M.p. 207–208° C.; $^1$H-NMR (CDCl$_3$) δ12.04 (br. s, 1H, NH), 4.45 (s, 2H, CH$_2$), 4.11 (s, 3H, OMe).

EXAMPLE 23

Preparation of N-{[(3-methoxy-1,2,4-thiadiaozol-5-yl) carbamoyl]methyl}-L-leucyl-L-proline methyl ester.

To a solution of 5-bromoacetamido-3-methoxy-[1,2,4] thiadiazole (0.76 g, 3 mmol) and L-leucine-L-proline methyl ester (0.97 g, 4 mmol) was added solid sodium iodide (45 mg, 0.3 mmol), tetrabutylammonium bromide (97 mg, 0.3 mmol) and triethylamine (0.7 mL, 5 mmol). The resulting mixture was stirred for 3 h, then quenched with brine and extracted into ethyl acetate. The organic layer was washed with a saturated solution of sodium bicarbonate, brine, dried (sodium sulfate), filtered and concentrated in vacuo. Purification by column chromatography on silica gel using a solvent mixture of hexane and ethyl acetate (1/1) followed by a mixture of dichloromethane and methanol (96/4) gave N-{[(3-methoxy-1,2,4-thiadiaozol-5-yl)carbamoyl] methyl}-L-leucyl-L-proline methyl ester as an off-white solid (1.09 g, 88%).M.p. 154–155° C.; MS (m/z) 414 (M$^+$+1), 382, 340, 257, 199, 130, 75.

EXAMPLE 24

Preparation of N-{[(3-methoxy-1,2,4-thiadiaozol-5-yl) carbamoyl]methyl}-L-leucyl-L-proline.

Base saponification N-{[(3-methoxy-1,2,4-thiadiaozol-5-yl)carbamoyl]methyl}-L-leucyl-L-proline methyl ester with a 1N sodium hydroxide solution followed by acidification with a 1N HCl solution similar to example 3h (B) afforded N-{[(3-methoxy-1,2,4-thiadiaozol-5-yl)carbamoyl] methyl}-L-leucyl-L-proline methyl ester (80% yield).M.p. 195–197° C. with decomposition; $^1$H-NMR (MeOD) δ4.63 (d, J=16.9 Hz, 1H, COCH$_2$), 4.41 (br. dd, 1H, CHCO$_2$H), 4.17 (d, J=17.1 Hz, 1H, COCH$_2$), 4.05 (m, 1H, CHCH$_2$), 4.00 (s, 3H, OMe), 3.48–3.70 (m, 2H, CH$_2$pro), 1.72–2.40 (m, 6H, 3CH$_2$), 0.92–1.03 (m, 7H, 2CH$_3$+CH); MS (m/z) 400 (M$^+$+1).

EXAMPLE 25

A. Preparation of acid addition salt of a compound of formula I.

To an ice-cooled suspension of β-N-{3-(α-hydroxybenzyl)-1,2,4-thiadiazol-5-yl}-glycinamide (60 mg, 0.22 mmol) in methanol (10 mL) was bubbled HCl gas for ca. 2 min as a light yellow solution resulted. The volume of the reaction mixture was reduced to ca. 2 mL by rotary evaporation and diethyl ether was added. The voluminous yellow precipitate of the hydrochloride salt was collected by filtration and dried at 50° C. under vacuum for 3 h (67 mg, 99.1%). 2-[3-(1-Hydroxy-1-phenylmethyl)-[1,2,4] thiadiazol-5-ylamino]-acetamide hydrochloride salt or β-N-{3-(α-hydroxybenzyl)-1,2,4-thiadiazol-5-yl}-glycinamide hydrochloride salt, white solid. $^1$H-NMR (MeOD) δ7.47–7.51 (m, 2H), 7.30–7.40 (m, 3H), 5.81 (s, 1H, αH), 4.19 (s, 2H, NCH$_2$).

B. In a similar manner, the following compounds were made:

2-[3-(3-Phenylallyl)-[1,2,4]thiadiazol-5-ylamino]-acetamide hydrochloride salt or β-N-{43-cinnamyl-1,2,4-thiadiazol-5-yl}glycinamide hydrochloride salt, white solid, 99% yield, m.p. 209.0–210.5° C. with decomposition.

2-[3-(1-Hydroxy-1-phenylmethyl)-[1,2,4]thiadiazol-5-ylamino]-acetamide hydrochloride salt or β-N-{3-(α-hydroxybenzyl)-1,2,4-thiadiazol-5-yl}-glycinamide hydrochloride salt, white solid, 99.1% yield. $^1$H-NMR (MeOD) d 7.47–7.51 (m, 2H), 7.30–7.40 (m, 3H), 5.81 (s, 1H, αH), 4.19 (s, 2H, NCH$_2$).

2-(3-n-Butoxy-[1,2,4]thiadiazol-5-ylamino)-acetamide hydrochloride salt or β-N-{3-n-butoxy-1,2,4-thiadiazol-5-yl}-glycinamide hydrochloride salt, white solid, 86.5% yield, m.p. foamed at 124° C. and melted at 178–190° C. with decomposition.

2-[3-(1H-Indol-3-ylmethyl)-[1,2,4]thiadiazol-5-ylamino]-acetamide hydrochloride salt, white solid, 97.8% yield, m.p. foamed at 125° C. and melted at 209.0–210.50C. with decomposition.

EXAMPLE 26

Inhibition of human rhinovirus protease (3C P) by compounds of formula I.

Human Rhinovirus protease (3Cp) was dissolved in 50 mM of potassium Phosphate pH 7.5, 0.25 mM EDTA, 10% glycerol at 0.13 mg/mL. The total assay volume was 500 micro liters and the assays were run at room temperature (RT) which was 23° C. Assay buffer contained 50 mM TRIS/HCl, pH 7.0, 1 mM EDTA, 100 mM NaCl, 0.005 mM DTT. Human Rhinovirus 3Cp substrate (3CpS: Bachem M-2075, Abz-Glu-Thr-Leu-Phe-Gln-Gly-Pro-Val-p-nitro-Phe-NH$_2$) was dissolved in 80 mM NaHCO$_3$, 15% DMSO. All inhibitors were dissolved in DMSO to 20 mM. All inhibitors were dissolved immediately prior to their assays. The enzyme 3Cp was added to the assay buffer to 0.007 mg/mL or 0.3 microM. The mixture was incubated at RT for 10–15 minutes. The reaction was initiated by the addition of 3Cp to 0.03 mM. When the inhibitors were assayed, they were added immediately after the addition of 3Cp. Fluorescence readings were recorded at 1 second intervals for 600 sec. The data were downloaded to a disk, uploaded as text file, and converted to dF vs time(s) values. The data were transfered to the program MacCurveFit and, fit to the linear equation y=mx+b, where y–dF, x=time and m=rate(dF/s). R2>0.97. Vo=steady-state rate (dF/s) without inhibitors. V$_i$=steady-state rate (dF/s) with inhibitor. % Inhibition=1–V$_i$/V$_o$.

N-{3-methoxy-1,2,4-thiadiazol-5-yl}-glycinamide; IC$_{50}$= 62 μM.

EXAMPLE 27

Inhibition of cathepsin B by 1,2,4-thiadiazoles. Enzyme assays and kinetic measurements.

Conditions for the above experiments can be found in the following references: Menard R. et al., 30 Biochemistry 1990, 29, 6706–6713; Fox T. et al., Biochemistry 1992, 31, 12571–12576; Cannona E. et al. Biochemistry 1996, 35, 8149–8157. A typical experiment consists in choosing an inhibitor concentration such that maximum inhibition could be achieved in less than two hours, monitoring the complete progress curve (i.e. fluorescence vs time), and analyzing the data. The analysis yield two parameters: the % inhibition once steady state was reached, and a rate constant which represents the rate at which this steady state is reached. Typically, the enzyme activity decreases with time until the maximum level of inhibition is reached (i.e. steady state) where the enzyme activity remains constant. Since significant levels of activity could still be detected at steady state (i.e. inhibition is not complete), the data was fitted to equation (1), which is normally used for slow-binding reversible inhibitors.

$$[P] = v_o \cdot t + \{(v_i - v_o \cdot)[1 - e^{-k_{obs} \cdot t}]\}/k_{obs} \quad (1)$$

$$\% \text{ inhibition} = (1 - v_i/v_o) \cdot 100 \quad (2)$$

In this equation, [P] represents the concentration of product (obtained from the flourescene readings), $k_{obs}$ is the first order rate constant to reach steady state, $v_o$ is the initial rate which corresponds to the rate in the absence of the inhibitor, and $v_i$ is the rate of the inhibited enzyme at steady state. The % inhibition was obtained by using equation (2), where the rate measured in the absence of the inhibitor was used for $v_o$. An example of a simple mechanism for such a process is given below:

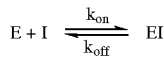

For this mechanism, the value of $k_{obs}$ determined experimentally would correspond to:

$$k_{obs} = k_{on}[inh] + k_{off}$$

The value of $k_{off}$ varies with inhibitor concentration. Often $k_{off}$ is much slower than $k_{on}[inh]$ and $k_{obs}/[inh]$ can be used to approximate $k_{on}$. This approach is used in this study and the results are shown in below:

3-methoxy-5-(carbobenzyloxy-L-phenylalanyl-L-alaninamido)-1,2,4-thiadiazole, 65% inhibition at 400 mM, $k_{obs}/[Inh]=38$ M$^{-1}$ s$^{-1}$.

N-[3-methoxy-{1,2,4}-thiadiazol-5-yl]-(L-leucyl-L-proline), 85% inhibition at 60 mM, $k_{obs}/[Inh]=170$ M$^{-1}$ s$^{-1}$.

EXAMPLE 28
Inhibition of transglutaminase by compounds of formula I (Enzyme Assay).

Transglutaminase activity is measured by the calorimetric hydroxamate procedure (J. Biol. Chem., 1971, 246, 1093). The tested compounds were dissolved in methanol and added to a buffered solution of purified Transglutaminase to give a final concentration of 0.1 mM (10% MeOH). After on hour of incubation, the solution was assayed for residual activity using the standard activity assay. 3-Methoxy-5-(carbobenzyloxy-L-phenylalanyl-L-alaninamido)-1,2,4-thiadiazole completely inhibits the enzyme at 100 $\mu$M.

EXAMPLE 29
Preparation of Pharmaceutically Acceptable Salt.

A solution of tris(hydroxymethyl)methylamine (61 mg, 0.5 mmol) in 2 mL water was added dropwise to a solution of N-{(3-methoxy)-[1,2,4]thiadiazol-5-yl}-L-leucyl-L-proline (171 mg, 0.5 mmol) in 10 mL methanol. The resulting clear solution was stirred for 1 h at room temperature. Volatile materials were removed in vacuo and the residual white foam was dried under vacuum at room temperature for 16 h (225 mg, yield 97.1%). M.p. foamed at 49° C. and melted at 127–128° C.; $^1$H-NMR (MeOD) δ4.80 (m, 1H, CHN), 4.30 (m, 1H, CHCO$_2$), 3.93 (s, 2H), 3.91 (s, 2H), 3.90 (s, 2H), 3.62 (s, 3H, OMe), 3.50–3.60 (m, 2H), 2.00–2.20 (m, 3H), 1.60–1.85 (m, 3H), 0.94–1.05 (m, 7H, 2Me and 2CH).

EXAMPLE 30
The effect of N-{(3-methoxy)-[1,2,4]thiadiazol-5-yl}-L-leucyl-L-proline tris(hydroxymethyl)methylamine salt (Apo501) on IL-1-Induced Proteoglycan Degradation.

The effect of Apo501 on IL-1 (interleukin) induced proteoglycan degradation of articular cartilage from normal calf joints was investigated in-vitro. Articular cartilage was sliced aseptically from the distal forelimb joints of less than 6-month old calves. The joint showed no clinical sign of skeletal disease. The cartilage was cut out with a sterile biopsy punch to the diameter of 3.5 mm with comparable thickness. The pooled, punched cartilage was washed and incubated in 20 ml of Ham's F12 medium with 5% FBS and 3% antibiotics for 72 hr at 37° C. for recovery.

Revoered explants were washed and replaced with a fresh medium. 20 $\mu$l (10 $\mu$Ci/ml) of sodium [$^{35}$S] sulfate was added and cartilage explants incubated for 72 h at 37° C. to radiolabel proteoglycans. The explants was washed thoroughly (5 times) to remove free radioisotope and incubated in serum free, F-12 medium (3% Ab) overnight. Explants were then incubated in quadruplicate in fresh, serum free mediums containing varied concentrations of Apo-501 ($10^{-7}$, $10^{-6}$, $10^{-5}$, and $10^{-4}$) for 24 h. On the next day, each cartilage was washed and transferred to a well in a 24-well plate, to which 1 ml of freshly prepared medium (serum-free, 3% Ab) that contains corresponding Apo-501 concentration and 50 ng of IL-β was added. The explants were incubated for 72 h at 37° C. The extent of proteoglycan degradation in each cartilage treated with different concentrations of Apo501 was determined by measuring the radioactivity of [$^{35}$S] sulfate-glycosaminoglycans by a liquid scintillation counter. Sample of 100 $\mu$l medium was added to 5 ml of scintillation cocktail (Ready Safe, Beckmann) and counted. Proteoglycan degradation was expressed as radiolabelled glycosaminoglycans released into the media (counts per min per ml) per dry weight (mg) of cartilage.

Figure 2:
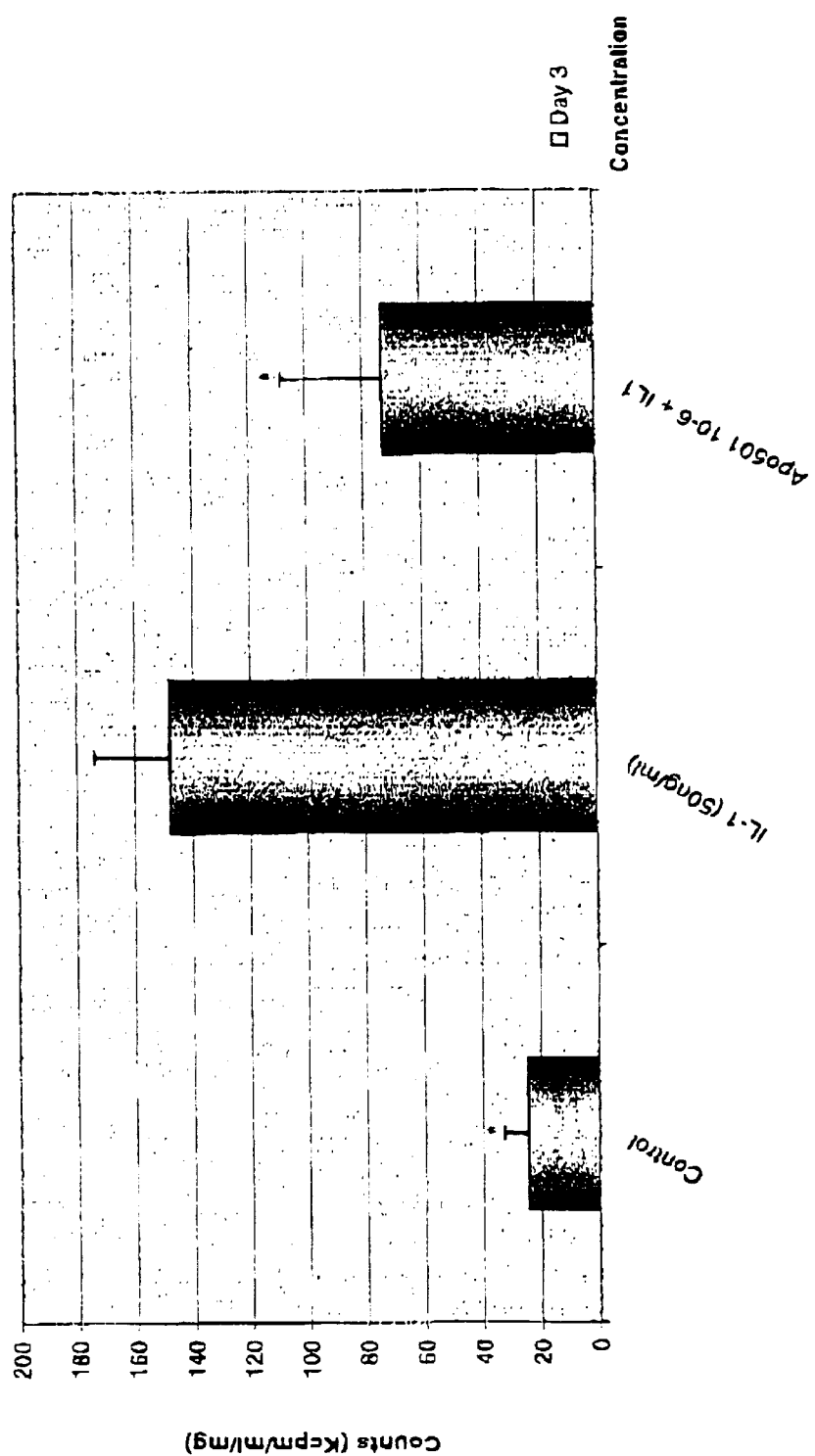
FIG. 2 is a diagrammatic representation of the reduction of IL-1-induced degradation of newly synthesized proteoglycan by a compound of formula (I).

As shown in FIG. 2, Apo501 demonstrated an inhibitory effect on the IL-1 induced proteoglycan degradation. Apo501 resulted in a significant reduction (60%) of IL-1 (50 ng/ml)-induced degradation of newly synthesized proteoglycan (p=0.023) at 1×10$^{-6}$ M.

What we claim is:

1. 3–5 disubstituted 1,2,4-thiadiazoles compounds, having the general formula (III):

(III)

or their pharmaceutically acceptable salts thereof, wherein A is an amino acid residue, or a peptide containing 2 to 3 amino acid residues with the N-terminal of A attached by the means of a spacer X to the C5 of the 1,2,4-thiadiazole ring, or an isosteric form thereof, X is a spacer selected from the group of formula

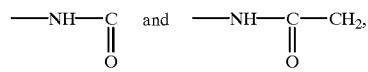

W represents a group of formula —N(R$^1$)$_2$ or —OR$^1$ with R$^1$ being independently hydrogen, lower alkyl, lower alkenyl, lower alkynyl in which the unsaturated bond is at least one carbon removed from the N or O atom;
and Y is selected from:
   (1) lower alkoxy, lower cycloalkoxy, lower arylalkoxy, heterocyclyloxy, and lower heterocyclylalkoxy wherein the alkyl or aryl ring is optionally substituted with 1 to 2 substituents selected from the group amino, alkoxy, hydroxy, halo, amino, alkylamino, dialkylamino;

(2) lower alkyl, lower cycloalkyl, lower heterocyclylalkyl, heterocyclyl, aryl, lower arylalkyl, lower arylalkenyl, lower heterocyclylalkenyl wherein the alkyl or aryl ring is optionally substituted with 1 to 2 substituents selected from the group amino, alkoxy, hydroxy, halo, amino, alkylamino, and dialkylamino;

(3) lower alkoxycarbonyl, carboxyl;

(4) a ketone group of formula:

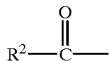

in which $R^2$ represents lower alkyl, lower cycloalkyl, lower heterocyclylalkyl, heterocyclyl, aryl, lower arylalkyl wherein the alkyl or aromatic ring is optionally substituted with 1 to 2 substituents selected from the group amino, alkoxy, hydroxy, halo, amino, alkylamino, dialkylamino;

(5) a carbamoyl group of formula:

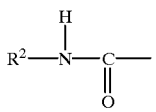

with $R^2$ being as defined above;

(6) amino, lower alkylamino, lower dialkylamino;

(7) amide of formula:

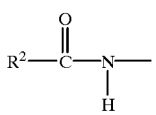

with $R^2$ being as defined above;

(8) a group of formula:

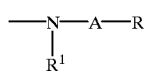

wherein A is as defined above and the carboxyl terminal of A is directly attached to the nitrogen of the 3-amino-1,2,4-thiadiazole. R and $R^1$ being as defined above;

(9) alcohol of formula:

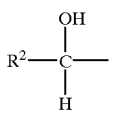

with $R^2$ being as defined above;

(10) sulfone of formula:

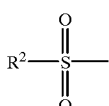

with $R^2$ being as defined above;

(11) sulfoxide of formula:

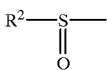

with $R^2$ being as defined above;

(12) sulfonamide of formula:

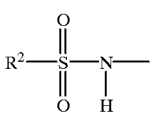

with $R^2$ being as defined above;

(13) lower alkylthio, lower arylalkylthio, arylthio;

(14) a group of formula:

with A as defined above and the N-terminal of A is directly attached to the methylene and W being as defined above;

(15) a group of formula:

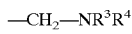

in which $R^3$ and $R^4$ are independently alkyl, aralkyl, heterocyclyl, heterocyclylalkyl; $R^3$ and $R^4$ when taken together form with the N-atom a five or a six membered ring selected from the group piperidinyl, pyrrolidinyl, piperazinyl with the N-4 position of piperazine optionally substituted with pyridyl, heterocyclyl, alkyl, aralkyl and aryl.

2. 3,5-disubstituted 1,2,4-thiadiazoles compounds, having the general formula (IV):

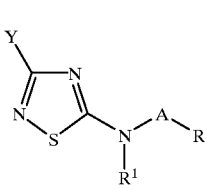

(IV)

or their pharmaceutically acceptable salts thereof, wherein A is an amino acid residue, or a peptide containing 2 to 3 amino acid residues, the carboxyl terminal of A is directly attached to the nitrogen of the 5-amino 1,2,4 thiadiazole and R represents hydrogen, lower alkanoyl, lower cycloalkylcarbonyl, lower alkoxycarbonyl, lower arylalkyloxycarbonyl or N-protecting group and R1 represents hydrogen, lower alkyl, lower alkenyl, lower alkynyl in which the unsaturated bond is at least one carbon removed from the N atom;

and Y is selected from:

(1) lower alkoxy, lower cycloalkoxy, lower arylalkoxy, heterocyclyloxy, and lower heterocyclylalkoxy wherein the alkyl or aryl ring is optionally substituted with 1 to 2 substituents selected from the group amino, alkoxy, hydroxy, halo, amino, alkylamino, dialkylamino;

(2) lower alkyl, lower cycloalkyl, lower heterocyclylalkyl, heterocyclyl, aryl, lower arylalkyl, lower arylalkenyl, lower heterocyclylalkenyl wherein the alkyl or aryl ring is optionally substituted with 1 to 2 substituents selected from the group amino, alkoxy, hydroxy, halo, amino, alkylamino, and dialkylamino;

(3) lower alkoxycarbonyl, carboxyl;

(4) a ketone group of formula:

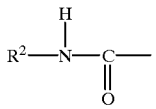

in which $R^2$ represents lower alkyl, lower cycloalkyl, lower heterocyclylalkyl, heterocyclyl, aryl, lower arylalkyl wherein the alkyl or aromatic ring is optionally substituted with 1 to 2 substituents selected from the group amino, alkoxy, hydroxy, halo, amino, alkylamino, dialkylamino;

(5) a carbamoyl group of formula:

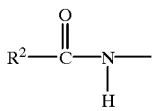

with $R^2$ being as defined above;

(6) amino, lower alkylamino, lower dialkylamino;

(7) amide of formula:

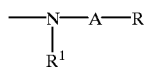

with $R^2$ being as defined above;

(8) a group of formula:

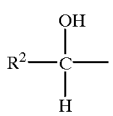

wherein A is as defined above and the carboxyl terminal of A is directly attached to the nitrogen of the 3-amino-1,2,4-thiadiazole. R and $R^1$ being as defined above;

(9) alcohol of formula:

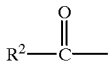

with $R^2$ being as defined above;

(10) sulfone of formula:

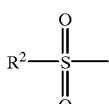

with $R^2$ being as defined above;

(11) sulfoxide of formula:

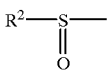

with $R^2$ being as defined above;

(12) sulfonamide of formula:

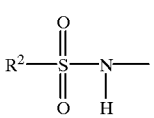

with $R^2$ being as defined above;

(13) lower alkylthio, lower arylalkylthio, arylthio;

(14) a group of formula:

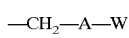

with A as defined above and the N-terminal of A is directly attached to the methylene and W being as defined above;

(15) a group of formula:

in which $R^3$ and $R^4$ are independently alkyl, aralkyl, heterocyclyl, heterocyclylalkyl; $R^3$ and $R^4$ when taken together form with the N-atom a five or a six membered ring selected from the group piperidinyl, pyrrolidinyl, piperazinyl with the N-4 position of piperazine optionally substituted with pyridyl, heterocyclyl, alkyl, aralkyl and aryl.

3. 3–5 disubstituted 1,2,4-thiazole compounds, having the general formula (I):

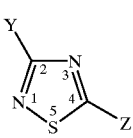

or their pharmaceutically acceptable salts thereof, wherein:

Z is selected from the groups:

(a) —A—W; in which A is a glycyl residue and W is $NH_2$;

(b) —X—A—W; in which X is a spacer selected from the groups of formula

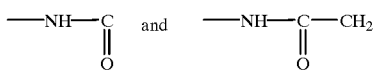

and A, W have the same definition as above;

(c)

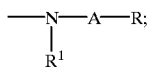

wherein R represents hydrogen, lower alkanoyl, lower cycloalkylcarbonyl, lower alkoxycarbonyl, lower arylalkyloxycarbonyl or N-protecting group and $R^1$ is hydrogen, lower alkyl, lower alkenyl, lower alkynyl in which the unsaturated bond is at least one carbon removed from the N atom, and A has the same definition as above; with the proviso that in groups (a) and (b), the N-terminal of A is either directly attached or by means of a spacer X as defined above to the C5 of the 1,2,4-thiadiazole ring respectively; and group (c), the carboxyl terminal of A is directly attached to the nitrogen of the 5-amino-1,2,4-thiadiazole;

and Y is selected from:

(1) lower alkoxy, lower cycloalkoxy, lower arylalkoxy, heterocyclyloxy, and lower heterocyclylalkoxy wherein the alkyl or aryl ring is optionally substituted with 1 to 2 substituents selected from the group amino, alkoxy, hydroxy, halo, amino, alkylamino, dialkylamino;

(2) lower alkyl, lower cycloalkyl, lower heterocyclylalkyl, heterocyclyl, aryl, lower arylalkyl, lower arylalkenyl, lower heterocyclylalkenyl wherein the alkyl or aryl ring is optionally substituted with 1 to 2 substituents selected from the group amino, alkoxy, hydroxy, halo, amino, alkylamino, and dialkylamino;

(3) lower alkoxycarbonyl, carboxyl;

(4) a ketone group of formula:

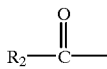

in which $R^2$ represents lower alkyl, lower cycloalkyl, lower heterocyclylalkyl, heterocyclyl, aryl, lower arylalkyl wherein the alkyl or aromatic ring is optionally substituted with 1 to 2 substituents selected from the group amino, alkoxy, hydroxy, halo, amino, alkylamino, dialkylamino;

(5) a carbamoyl group of formula:

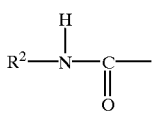

with $R^2$ being as defined above;

(6) amino, lower alkylamino, lower dialkylamino;

(7) amide of formula:

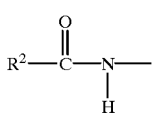

with $R^2$ being as defined above;

(8) a group of formula:

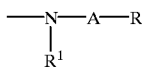

wherein A is as defined above and the carboxyl terminal of A is directly attached to the nitrogen of the 3-amino-1,2,4-thiadiazole, R and $R^1$ being as defined above;

(9) alcohol of formula:

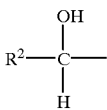

with $R^2$ being as defined above;

(10) sulfone of formula:

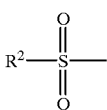

with $R^2$ being as defined above;

(11) sulfoxide of formula:

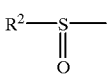

with $R^2$ being as defined above;

(12) sulfonamide of formula:

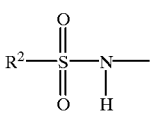

with $R^2$ being as defined above;

(13) lower alkylthio, lower arylalkylthio, arylthio;

(14) a group of formula:

with A as defined above and the N-terminal of A is directly attached to the methylene and W being as defined above;

(15) a group of formula:

in which $R^3$ and $R^4$ are independently alkyl, aralkyl, heterocyclyl, heterocyclylalkyl; $R^3$ and $R^4$ when taken together form with the N-atom a five or a six membered ring selected from the group piperidinyl, pyrrolidinyl, piperazinyl with the N-4 position of piperazine optionally substituted with pyridyl, heterocyclyl, alkyl, aralkyl and aryl.

4. 3–5 disubstituted 1,2,4-thiadiazole compounds, having the general formula (II):

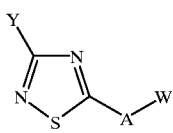
(II)

or their pharmaceutically acceptable salts thereof, wherein A is a glycyl residue and W represents NH$_2$;
and Y is selected from:

(1) lower alkoxy, lower cycloalkoxy, lower arylalkoxy, a heterocyclyloxy, and lower heterocyclylalkoxy wherein the alkyl or aryl ring is optionally substituted with 1 to 2 substituents selected from the group amino, alkoxy, hydroxy, halo, amino, alkylamino, dialkylamino;

(2) lower alkyl, lower cycloalkyl, lower heterocyclylalkyl, heterocyclyl, aryl, lower arylalkyl, lower arylalkenyl, lower heterocyclylalkenyl wherein the alkyl or aryl ring is optionally substituted with 1 to 2 substituents selected from the group amino, alkoxy, hydroxy, halo, amino, alkylamino, and dialkylamino;

(3) lower alkoxycarbonyl, carboxyl;

(4) a ketone group of formula:

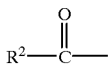

in which R$^2$ represents lower alkyl, lower cycloalkyl, lower heterocyclylalkyl, heterocyclyl, aryl, lower arylalkyl wherein the alkyl or aromatic ring is optionally substituted with 1 to 2 substituents selected from the group amino, alkoxy, hydroxy, halo, amino, alkylamino, dialkylamino;

(5) a carbamoyl group of formula:

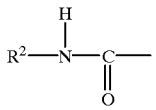

with R$^2$ being as defined above;

(6) amino, lower alkylamino, lower dialkylamino;

(7) amide of formula:

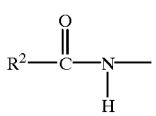

with R$^2$ being as defined above;

(8) a group of formula:

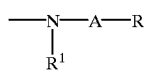

wherein A is as defined above and the carboxyl terminal of A is directly attached to the nitrogen of the 3-amino-1,2,4-thiadiazole, R represents hydrogen, lower alkanoyl, lower cycloalkylcarbonyl, lower alkoxycarbonyl, lower arylalkyloxycarbonyl or N protecting group and R$^1$ is hydrogen, lower alkyl, lower alkenyl, lower alkynyl in which the unsaturated bond is at least one carbon removed from the N atom;

(9) alcohol of formula:

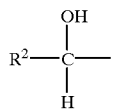

with R$^2$ being as defined above;

(10) sulfone of formula:

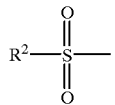

with R$^2$ being as defined above;

(11) sulfoxide of formula:

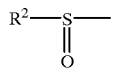

with R$^2$ being as defined above;

(12) sulfonamide of formula:

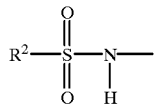

with R$^2$ being as defined above;

(13) lower alkylthio, lower arylalkylthio, arylthio;

(14) a group of formula:

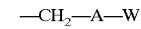

—CH$_2$—A—W with A as defined above and the N-terminal of A is directly attached to the methylene and W being as defined above;

(15) a group of formula:

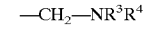

—CH$_2$—NR$^3$R$^4$ in which R$^3$ and R$^4$ are independently alkyl, aralkyl, heterocyclyl, heterocyclylalkyl; R$^3$ and R$^4$ when taken together form with the N-atom a five or a six membered ring selected from the group piperidinyl, pyrrolidinyl, piperazinyl with the N-4 position of piperazine optionally substituted with pyridyl, heterocyclyl, alkyl, aralkyl and aryl.

5. A compound according to claim 3 or 4 is methoxy, which is N-(3-methoxy-[1,2,4]thiadiazol-5-ylamino)-acetamide.

6. A compound according to claim 3 or 4 wherein Y is n-butoxyl) which is N-(3-n-Butoxy-[1,2,4]thiadiazol-5-ylamino)-acetamide.

7. A compound according to claim 3 or 4 wherein Y is cinnamyl) which is N-(3-Phenylallyl)-[[1,2,4]thiadiazol-5-ylamino]-acetamide.

8. A compound according to claim 3 or 4 wherein Y is 1-H-Indol-3-ylmethyl) which is N-{3-(1H-Indol-3-ylmethyl)-[1,2,4]thiadiazol-5-ylamino]}-acetamide.

9. 3–5 disubstituted 1,2,4-thiazole compounds, having the general formula (I):

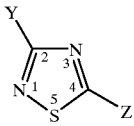
(I)

or their pharmaceutically acceptable salts thereof, wherein:
Z is selected from the groups:
(a) —A—W; in which A is either leucyl-propyl or isoleucyl-propyl and W is —OH;
(b) —X—A—W; in which X is a spacer selected from the groups of formula

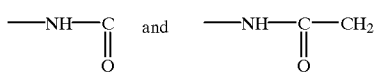

and A, W have the same definition as above;
(c)

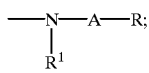

wherein R represents hydrogen, lower alkanoyl, lower cycloalkylcarbonyl, lower alkoxycarbonyl, lower arylalkyloxycarbonyl or N-protecting group and $R^1$ is hydrogen, lower alkyl, lower alkenyl, lower alkynyl in which the unsaturated bond is at least one carbon removed from the N atom, and A has the same definition as above;

with the proviso that in:
groups (a) and (b), the N-terminal of A is either directly attached or by means of a spacer X as defined above to the C5 of the 1,2,4-thiadiazole ring respectively; and
group (c), the carboxyl terminal of A is directly attached to the nitrogen of the 5-amino-1,2,4-thiadiazole;
and Y is selected from:

(1) lower alkoxy, lower cycloalkoxy, lower arylalkoxy, heterocyclyloxy, and lower heterocyclylalkoxy wherein the alkyl or aryl ring is optionally substituted with 1 to 2 substituents selected from the group amino, alkoxy, hydroxy, halo, amino, alkylamino, dialkylamino;

(2) lower alkyl, lower cycloalkyl, lower heterocyclylalkyl, heterocyclyl, aryl, lower arylalkyl, lower arylalkenyl, lower heterocyclylalkenyl wherein the alkyl or aryl ring is optionally substituted with 1 to 2 substituents selected from the group amino, alkoxy, hydroxy, halo, amino, alkylamino, and dialkylamino;

(3) lower alkoxycarbonyl, carboxyl;
(4) a ketone group of formula:

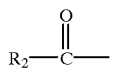

in which $R^2$ represents lower alkyl, lower cycloalkyl, lower heterocyclylalkyl, heterocyclyl, aryl, lower arylalkyl wherein the alkyl or aromatic ring is optionally substituted with 1 to 2 substituents selected from the group amino, alkoxy, hydroxy, halo, amino, alkylamino, dialkylamino;

(5) a carbamoyl group of formula:

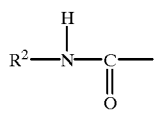

with $R^2$ being as defined above;
(6) amino, lower alkylamino, lower dialkylamino;
(7) amide of formula:

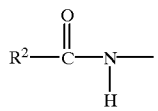

with $R^2$ being as defined above;
(8) a group of formula:

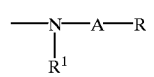

wherein A is as defined above and the carboxyl terminal of A is directly attached to the nitrogen of the 3-amino-1,2,4-thiadiazole, R and $R^1$ being as defined above;

(9) alcohol of formula:

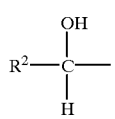

with $R^2$ being as defined above;
(10) sulfone of formula:

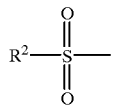

with $R^2$ being as defined above;

(11) sulfoxide of formula:

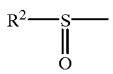

with $R^2$ being as defined above;

(12) sulfonamide of formula:

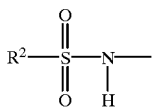

with $R^2$ being as defined above;

(13) lower alkylthio, lower arylalkylthio, arylthio;

(14) a group of formula:

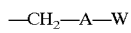

with A as defined above and the N-terminal of A is directly attached to the methylene and W being as defined above;

(15) a group of formula:

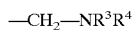

in which $R^3$ and $R^4$ are independently alkyl, aralkyl, heterocyclyl, heterocyclylalkyl; $R^3$ and $R^4$ when taken together form with the N-atom a five or a six membered ring selected from the group piperidinyl, pyrrolidinyl, piperazinyl with the N-4 position of piperazine optionally substituted with pyridyl, heterocyclyl, alkyl, aralkyl and aryl.

10. 3–5 disubstituted 1,2,4-thiadiazole compounds, having the general formula (II):

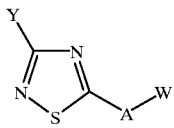

or their pharmaceutically acceptable salts thereof, wherein A is leucyl-propyl or isoleucyl-propyl and W is —OH; and Y is selected from:

(1) lower alkoxy, lower cycloalkoxy, lower arylalkoxy, heterocyclyloxy, and lower heterocyclylalkoxy wherein the alkyl or aryl ring is optionally substituted with 1 to 2 substituents selected from the group amino, alkoxy, hydroxy, halo, amino, alkylamino, dialkylamino;

(2) lower alkyl, lower cycloalkyl, lower heterocyclylalkyl, heterocyclyl, aryl, lower arylalkyl, lower arylalkenyl, lower heterocyclylalkenyl wherein the alkyl or aryl ring is optionally substituted with 1 to 2 substituents selected from the group amino, alkoxy, hydroxy, halo, amino, alkylamino, and dialkylamino;

(3) lower alkoxycarbonyl, carboxyl;

(4) a ketone group of formula:

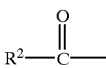

in which $R^2$ represents lower alkyl, lower cycloalkyl, lower heterocyclylalkyl, heterocyclyl, aryl, lower arylalkyl wherein the alkyl or aromatic ring is optionally substituted with 1 to 2 substituents selected from the group amino, alkoxy, hydroxy, halo, amino, alkylamino, dialkylamino;

(5) a carbamoyl group of formula:

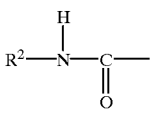

with $R^2$ being as defined above;

(6) amino, lower alkylamino, lower dialkylamino;

(7) amide of formula:

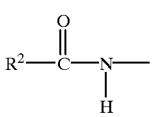

with $R^2$ being as defined above;

(8) a group of formula:

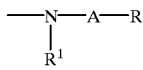

wherein A is as defined above and the carboxyl terminal of A is directly attached to the nitrogen of the 3-amino-1,2,4-thiadiazole, R represents hydrogen, lower alkanoyl, lower cycloalkylcarbonyl, lower alkoxycarbonyl, lower arylalkyloxycarbonyl or N protecting group and $R^1$ is hydrogen, lower alkyl, lower alkenyl, lower alkynyl in which the unsaturated bond is at least one carbon removed from the N atom;

(9) alcohol of formula:

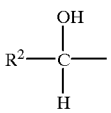

with $R^2$ being as defined above;

(10) sulfone of formula:

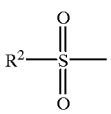

with $R^2$ being as defined above;

(11) sulfoxide of formula:

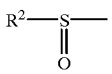

with $R^2$ being as defined above;

(12) sulfonamide of formula:

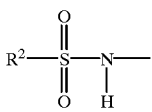

with $R^2$ being as defined above;

(13) lower alkylthio, lower arylalkylthio, arylthio;

(14) a group of formula:

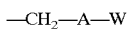

with A as defined above and the N-terminal of A is directly attached to the methylene and W being as defined above;

(15) a group of formula:

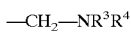

in which $R^3$ and $R^4$ are independently alkyl, aralkyl, heterocyclyl, heterocyclylalkyl; $R^3$ and $R^4$ when taken together form with the N-atom a five or a six membered ring selected from the group piperidinyl, pyrrolidinyl, piperazinyl with the N-4 position of piperazine optionally substituted with pyridyl, heterocyclyl, alkyl aralkyl and aryl.

11. Compounds according to claim 9 or 10 wherein A is leucyl-prolyl.

12. Compounds according to claim 9 or 10 wherein A is isoleucyl-prolyl.

13. A compound according to claim 11 wherein Y is methoxy, which is N-(3-methoxy-[1,2,4]thiadiazol-5-yl)-L-leucyl-L-proline.

14. A compound according to claim 11 wherein Y is n-butoxy, which is N-(3-Butoxy-[1,2,4]thiadiazol-5-yl)-L-leucyl-L-proline.

15. A compound according to claim 11 wherein Y is methyl, which is N-(3-Methyl-[1,2,4]thiadiazol-5-yl)-L-leucyl-L-proline.

16. A compound according to claim 11 wherein Y is phenyl, which is N-(3-Phenyl-[1,2,4]thiadiazol-5-yl)-L-leucyl-L-proline.

17. A compound according to claim 12 wherein Y is methoxy, which is N-(3-methoxy-[1,2,4]thiadiazol-5-yl)-L-isoleucyl-L-proline.

18. A compound according to claim 9 or 10 which is N,N'{3-methylene-[1,2,4]thiadiazol-5-yl}-di-{L-leucyl-L-proline}.

19. A compound according to claim 9 or 10 which is {3-[4-(2-pyridyl)piperazinylmethyl]-1,2,4-thiadiazol-5-yl}-leucyl-proline.

20. A compound according to claim 9 or 10 which is N,N'-{3-methylene-[1,2,4]thiadiazol-5-yl}-di{L-leucyl-L-proline methyl ester}.

21. Compounds according to claim 1 wherein X is

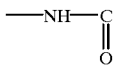

22. Compounds according to claim 1 wherein X is

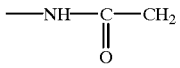

23. Compounds according to claim 21 wherein A is leucyl.

24. Compounds according to claim 23 wherein W is NH-isoamyl.

25. A compound according to claim 24 wherein Y is methoxy, which is 5-{3-methoxy-1,2,4-thiadiazolyl}carbamoyl-isoleucyl isoamylamide.

26. Compounds according to claim 22 wherein A is leucyl-prolyl.

27. A compound according to claim 26 wherein W is OH.

28. A compound according to claim 26 wherein W is methoxy, which is N-{(3-methoxy-[1,2,4]-thiadiazol-5-yl)carbamoylmethyl}-L-leucine-L-proline.

29. Compounds according to claim 2 wherein A is phenylalanyl, $R^1$ is hydrogen, and R is carbobenzyloxy.

30. A compound according to claim 29 wherein Y is methoxy, which is 5-(N-carbobenzyloxy-L-phenylalaninamido)-3-methoxy-[1,2,4]thiadiazole.

31. A compound according to claim 29 wherein Y is carbobenzyloxy-phenylalanimamido, which is N,N'-{3,5-di-(N-carbobenzyloxy-L-phenylalaninamido)}-[1,2,4]thiadiazole.

32. A pharmaceutical composition comprising a compound according to claim 3 or 4 or a pharmaceutically acceptable salt thereof together with a pharmaceutically acceptable diluent or carrier thereof.

33. A pharmaceutical composition comprising a compound according to claim 9 or 10 or a pharmaceutically acceptable salt thereof together with a pharmaceutically acceptable diluent or carrier thereof.

34. A pharmaceutical composition comprising a compound according to claim 1 or a pharmaceutically acceptable salt thereof together with a pharmaceutically acceptable diluent or carrier thereof.

35. A pharmaceutical composition comprising a compound according to claim 2 or a pharmaceutically acceptable salt thereof together with a pharmaceutically acceptable diluent or carrier thereof.

36. A method for treating a mammal with a disease or disorder, wherein said disease or disorder is ameliorated by inhibiting at least a cysteine activity dependent enzyme, which comprises a administering an effective amount of a compound of claim 3 or 4 or a pharmaceutically acceptable salt thereof.

37. A method for treating a mammal with a disease or disorder, wherein said disease or disorder is ameliorated by inhibiting at least a cysteine activity dependent enzyme, which comprises administering an effective amount of a compound of claim 9 or 10, or a pharmaceutically acceptable salt thereof.

38. A method for treating a mammal with a disease or disorder, wherein said disease or disorder is ameliorated by inhibiting at least a cysteine activity dependent enzyme, which comprises administering an effective amount of a compound of claim 1, or a pharmaceutically acceptable salt thereof.

39. A method for treating a mammal with a disease or disorder, wherein said disease or disorder is ameliorated by inhibiting at least a cysteine activity dependent enzyme, which comprises administering an effective amount of a compound of claim 2, or a pharmaceutically acceptable salt thereof.

40. The method of claims 38 or 39, wherein the disorder is acne.

41. The method of one of claims 38 or 39, wherein the disease is common cold.

42. The method of one of claims 38 or 39, wherein the disease is inflammatory joint disease.

\* \* \* \* \*

UNITED STATES PATENT AND TRADEMARK OFFICE
CERTIFICATE OF CORRECTION

PATENT NO. : 6,162,791  Page 1 of 1
DATED : December 19, 2000
INVENTOR(S) : Karimian et al.

It is certified that error appears in the above-identified patent and that said Letters Patent is hereby corrected as shown below:

Column 36,
Line 57, "R1" should read -- $R^1$ --;

Column 39,
Line 39, 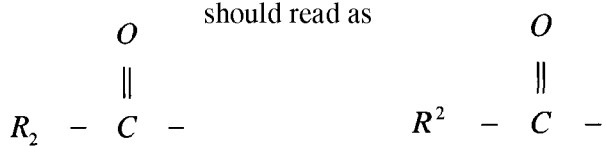 should read as

Column 43,
Line 21, "leucyl-propyl" should read -- leucyl-prolyl --;
Line 22, "isoleucyl-propyl" should read -- isoleucyl-prolyl --;

Column 44,
Line 7, 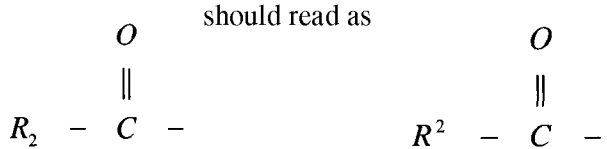 should read as

Column 45,
Line 52, "leucyl-propyl" should read -- leucyl-prolyl --; and
Line 52, "isoleucyl-propyl" should read -- isoleucyl-prolyl --.

Signed and Sealed this

Eighteenth Day of November, 2003

JAMES E. ROGAN
*Director of the United States Patent and Trademark Office*